US011633196B2

(12) United States Patent
Walker

(10) Patent No.: US 11,633,196 B2
(45) Date of Patent: Apr. 25, 2023

(54) MINIMALLY INVASIVE HIP ARTHROPLASTY TECHNIQUES AND APPARATUS

(71) Applicant: PMSW RESEARCH PTY LTD, Bellevue Hill (AU)

(72) Inventor: Peter Walker, Bellevue Hill (AU)

(73) Assignee: PMSW RESEARCH PTY LTD, Bellevue Hill (AU)

( * ) Notice: Subject to any disclaimer, the term of this patent is extended or adjusted under 35 U.S.C. 154(b) by 438 days.

(21) Appl. No.: 15/733,275

(22) PCT Filed: Dec. 21, 2018

(86) PCT No.: PCT/AU2018/051375
§ 371 (c)(1),
(2) Date: Jun. 19, 2020

(87) PCT Pub. No.: WO2019/119052
PCT Pub. Date: Jun. 27, 2019

(65) Prior Publication Data
US 2021/0093332 A1    Apr. 1, 2021

(30) Foreign Application Priority Data

Dec. 21, 2017   (AU) .................... 2017905106

(51) Int. Cl.
*A61B 17/17*  (2006.01)
*A61B 17/16*  (2006.01)
(Continued)

(52) U.S. Cl.
CPC .... *A61B 17/1746* (2013.01); *A61B 17/00234* (2013.01); *A61B 17/025* (2013.01);
(Continued)

(58) Field of Classification Search
CPC ............ A61B 17/1735; A61B 17/1742; A61B 17/1746; A61B 17/175; A61B 17/164;
(Continued)

(56) References Cited

U.S. PATENT DOCUMENTS 3,709,218 A * 1/1973 Halloran ................ A61B 17/72
606/71
4,549,319 A * 10/1985 Meyer ................... A61F 2/4603
606/100
(Continued)

OTHER PUBLICATIONS

International Search Report dated Feb. 8, 2019 from PCT Application No. PCT/AU2018/051375.

*Primary Examiner* — Matthew J Lawson
(74) *Attorney, Agent, or Firm* — Innovation Capital Law Group, LLP; Vic Lin

(57) ABSTRACT

A minimally invasive hip arthroplasty technique involves intramedullary insertion of an elongate femoral broach into a femur. The broach has a superior lateromedial transverse bore. A reaming rod is then located through the transverse bore and the neck of the femur. A cutting head is coupled to a distal end of the reaming rod via an incision. An orthogonal drive arm of an arthroplasty jig may also be inserted behind the cutting head to press the cutting head to ream the acetabulum while the reaming rod rotates the cutting head.

31 Claims, 36 Drawing Sheets

(51) Int. Cl.
*A61F 2/46* (2006.01)
*A61B 17/00* (2006.01)
*A61B 17/02* (2006.01)
*A61B 17/92* (2006.01)

(52) U.S. Cl.
CPC ........ *A61B 17/164* (2013.01); *A61B 17/1642* (2013.01); *A61B 17/1666* (2013.01); *A61B 17/1668* (2013.01); *A61B 17/175* (2013.01); *A61B 17/921* (2013.01); *A61F 2/4607* (2013.01); *A61F 2/4684* (2013.01); *A61B 2017/00353* (2013.01); *A61B 2017/0275* (2013.01); *A61B 2017/922* (2013.01); *A61F 2002/4635* (2013.01)

(58) Field of Classification Search
CPC ............ A61B 17/1664; A61B 17/1666; A61B 17/1668; A61B 17/1659; A61F 2/4607; A61F 2/32; A61F 2002/3208–3241; A61F 2/36–3676; A61F 2002/3601–3698
See application file for complete search history.

(56) References Cited

U.S. PATENT DOCUMENTS

| | | | |
|---|---|---|---|
| 4,587,964 A * | 5/1986 | Walker | A61B 17/1659 606/85 |
| 4,739,750 A | 4/1988 | Masse et al. | |
| 4,921,493 A * | 5/1990 | Webb, Jr. | A61B 17/1659 606/85 |
| 6,706,073 B2 * | 3/2004 | Draenert | A61F 2/4607 623/23.26 |
| 6,755,865 B2 | 6/2004 | Tarabishy | |
| 7,105,028 B2 * | 9/2006 | Murphy | A61B 17/56 623/22.4 |
| 7,582,090 B2 * | 9/2009 | Penenberg | A61F 2/4601 606/86 R |
| 7,695,474 B2 * | 4/2010 | Crofford | A61F 2/4657 606/81 |
| 9,610,084 B2 | 4/2017 | Walker | |
| 2003/0060889 A1 * | 3/2003 | Tarabishy | A61B 17/1617 623/22.17 |
| 2003/0130741 A1 | 7/2003 | McMinn | |
| 2005/0049602 A1 * | 3/2005 | Honl | A61B 17/175 606/86 R |
| 2005/0234463 A1 * | 10/2005 | Hershberger | A61F 2/3662 606/85 |
| 2006/0200160 A1 | 9/2006 | Border et al. | |
| 2010/0331992 A1 * | 12/2010 | Podolsky | A61B 17/1664 623/22.15 |
| 2011/0054550 A1 * | 3/2011 | Metzinger | A61B 17/72 606/86 R |
| 2012/0130502 A1 * | 5/2012 | Podolsky | A61B 17/7266 623/22.4 |
| 2012/0226361 A1 | 9/2012 | Podolsky | |
| 2014/0031948 A1 * | 1/2014 | Birmingham | A61B 17/1666 623/22.15 |
| 2014/0107652 A1 * | 4/2014 | Walker | A61B 17/15 606/81 |
| 2017/0135704 A1 * | 5/2017 | Abbasi | A61B 17/1637 |
| 2018/0078299 A1 * | 3/2018 | Rossney | A61B 17/725 |
| 2019/0038326 A1 * | 2/2019 | Hedgeland | A61B 17/1721 |
| 2021/0068979 A1 * | 3/2021 | Podolsky | A61B 17/1746 |
| 2022/0183857 A1 * | 6/2022 | Siccardi | A61B 17/1746 |

\* cited by examiner

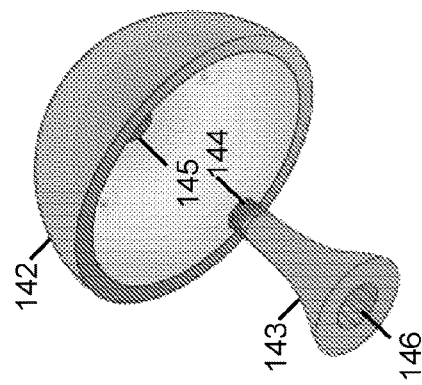
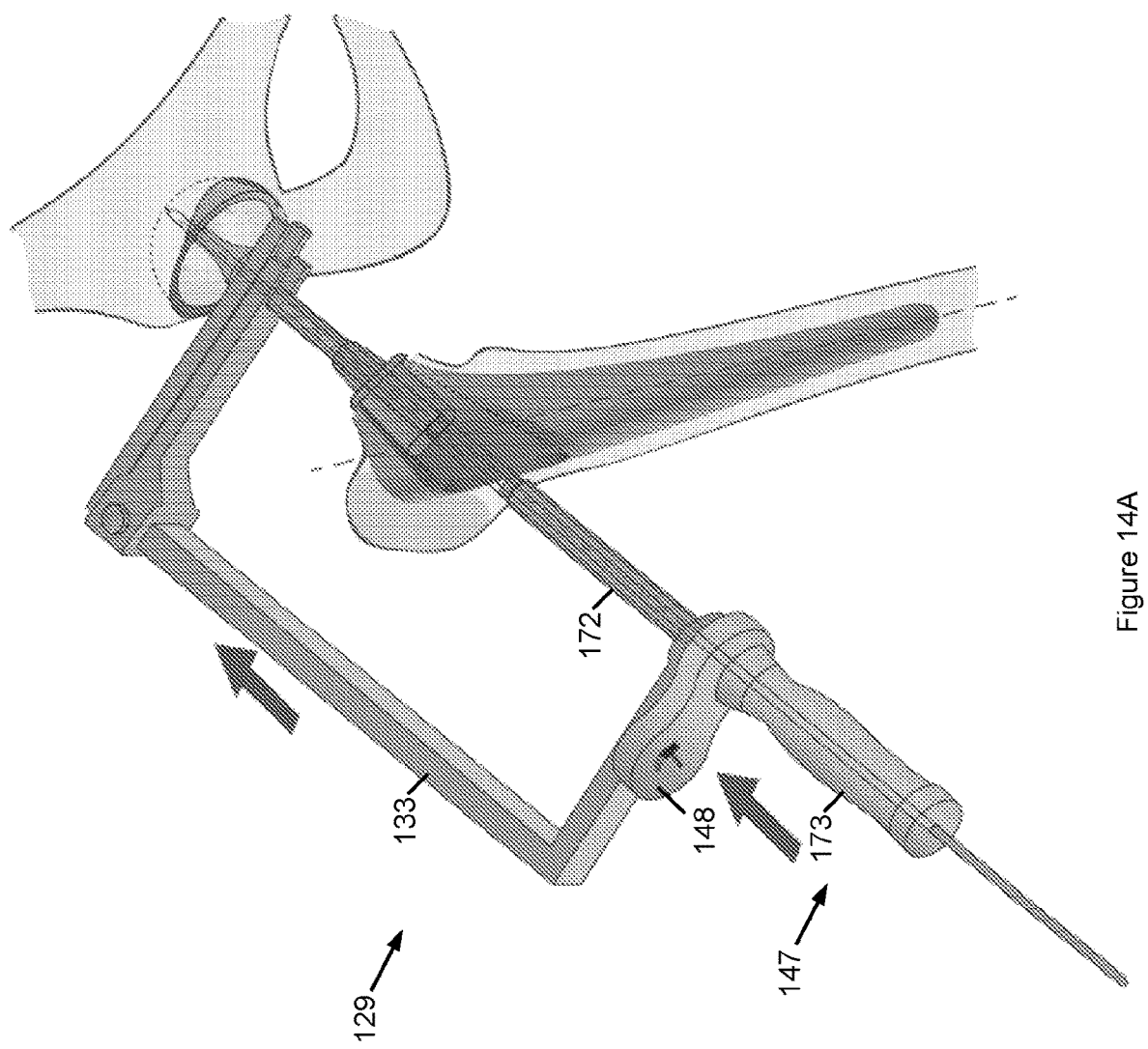
Figure 14B
Figure 14A

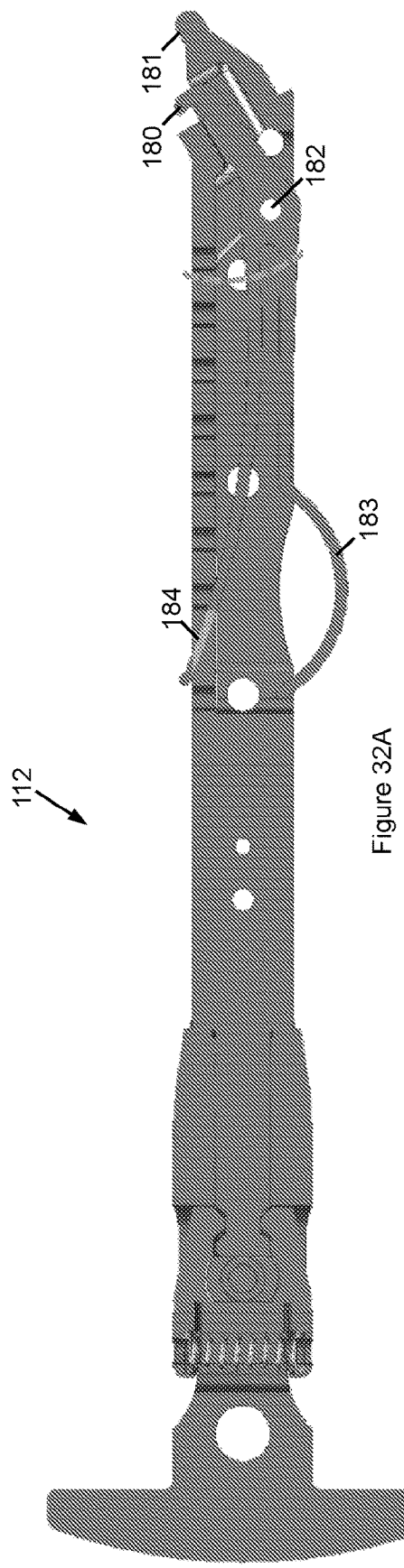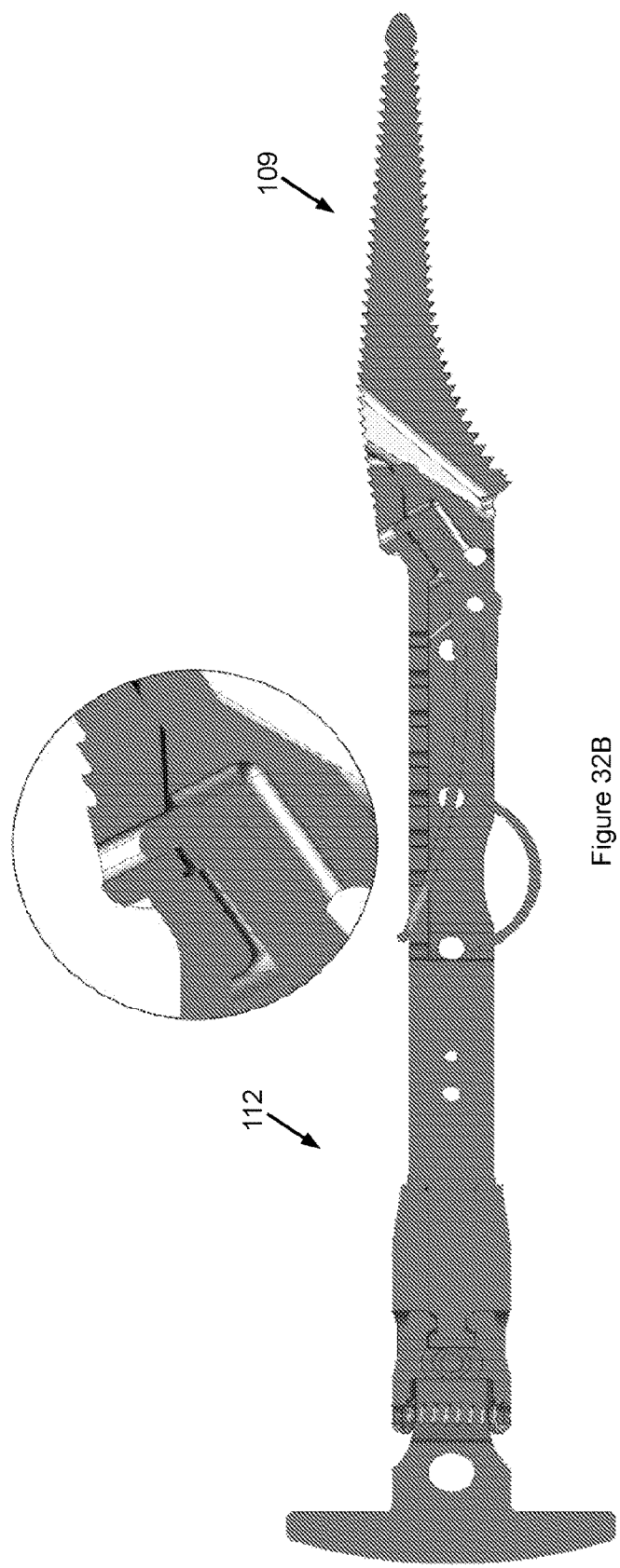
Figure 32A
Figure 32B

MINIMALLY INVASIVE HIP ARTHROPLASTY TECHNIQUES AND APPARATUS

FIELD OF THE INVENTION

This invention relates generally to minimally invasive hip arthroplasty techniques and apparatus. More particularly, this invention relates to techniques and apparatus for joint arthroplasty which minimises substantial retraction for femoral dislocation and associated iatrogenic soft tissue trauma as is associated with certain prior art arrangements.

BACKGROUND OF THE INVENTION

There are numerous ways to perform a joint arthroplasty, but which all share the same goal of replacement of the dysfunctional arthritic joint and replacing with materials that preserve joint function. Hip arthroplasty treatments or procedures are intended to provide a pain-free weight bearing joint whose motion replicates the native hip joint.

Arthroplasty procedures of the hip joint specifically target disease of the femoral head (ball portion) and acetabulum (socket portion). Traditional total hip replacement surgery excises the femoral head and a portion of the femoral neck as well as reaming (preparing) the acetabulum.

Surgical techniques to accomplish arthroplasty goals are typically open techniques which require direct visualization of the hip joint and therefore significant iatrogenic soft tissue trauma. Minimally invasive techniques used in arthroplasty surgery are typically made from the anterior aspect of the thigh, using one or two incisions. All techniques require the femoral neck to be cut and the femur retracted away from the acetabulum for reaming of the acetabulum.

Other superior minimally invasive approaches use angled reamers to avoid hip dislocation, but still require some retraction of the femur. Such retraction requires release of soft tissue and the associated iatrogenic damage to allow the tools to be inserted for preparation of the acetabulum and associated prosthesis.

For example, U.S. Patent Publication No. 2003/0130741, published Jul. 10, 2003 to McMinn, discloses a method of resurfacing a hip joint using a first incision made at the patient's hip joint, and a second incision made at the outer side of the patient's thigh. In particular, McMinn first teaches that a guide wire is installed through the second incision up and into the femoral head and neck. Following insertion of the guide wire, McMinn next teaches that the femoral head is dislocated from the acetabulum. With the femoral head dislocated, the guide wire is then over-drilled to produce a canal through the femoral neck exiting the zenith of the femoral head. Using a drive rod inserted through the second incision and up the femoral canal, the periphery of the femoral head is resected using a sleeve cutter inserted through the first incision.

A sleeve resection guide inserted through the first incision is then utilized to resect an appropriate amount of the zenith of the femoral head using a cutting blade. A chamfer cutter, inserted through the first incision, is then utilized to cut the femoral head to provide a chamfer thereon. Once the femoral head has been prepared, an acetabular reamer is inserted through the first incision and connected to the drive rod. The acetabular reamer can then be utilized to ream the acetabulum. McMinn then teaches the installation of an acetabular cup and femoral component are implanted.

By way of another example, U.S. Pat. No. 7,695,474, granted Apr. 13, 2010 to Crofford, discloses a method of resurfacing a hip joint using a femoral neck fixation prosthesis. Crofford discloses that an artificial femoral head is attached to a fixation prosthesis, which extends coaxially through a femoral canal formed in the femoral neck, into the femur, and is then attached to the opposite lateral wall of the femur. Crofford further teaches that the implantation of the femoral neck fixation prosthesis is accomplished by resecting the femoral head, reaming at least one passage in the femoral neck, reaming the acetabulum, and implanting the femoral neck fixation prosthesis into the reamed passage. Crofford further discloses that access to the femoral head and neck is accomplished by dislocating the femoral head from the acetabulum and rotating the leg of the patient to expose the head and neck.

One drawback of the method taught in McMinn and Crofford is the explicit requirement that the hip be dislocated during the procedure in order to expose the femoral head and neck. In particular, while hip dislocation during hip arthroplasty surgery is beneficial to expose the femoral head and neck, such may cause significant soft tissue damage that may prolong patient recovery time and increase the probability of postoperative complications. Accordingly, there is a need in the art for improved methods and apparatus for arthroplasty treatments using minimally invasive techniques which lower the risk of iatrogenic injury, postoperative complications, and provide improved means for performing hip treatments and procedures.

US publication 20120226361 A1 by Podolsky utilises a femoral inter-medullary rod which is inserted longitudinally into the femur. A prosthetic femoral neck is then inserted through a pre-existing lateral bore of the rod to join the prosthetic femoral head. However, Podolsky similarly teaches conventional reaming of the acetabulum (see paragraph 117).

U.S. Pat. No. 6,755,865 to Tarabishy discloses a segmented shell comprising separate parts which are inserted through a lateromedial femoral drillhole for assembly at a medial side thereof.

Tarabishy teaches the insertion of a drill having expandable blades through the lateromedial femoral drillhole for preparing the acetabulum.

U.S. Pat. No. 9,610,084 to Walker discloses hip replacement method which involves preparing a femoral neck passage lateromedially along an axis of a femoral neck of the femur using a guide wire. An elongate rod (typically of 10-15 mm in diameter) follows the guide wire to drive an acetabulum reamer to ream the acetabulum without dislocating the joint.

The present invention seeks to provides enhanced apparatus and methodology, which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art.

SUMMARY OF THE DISCLOSURE

There is disclosed herein minimally invasive arthroplasty techniques and apparatus which, in embodiments may minimize trauma and furthermore, in embodiments, may increase component placement accuracy. The techniques and apparatus disclosed herein will be specifically described with reference to hip arthroplasty but, as alluded to above, could be applied to other joints also with appropriate modification within the scope of the invention disclosed herein.

Hip replacement generally involves cutting of the femoral neck to remove the head and neck portion of the femur and the insertion of a femoral component into the femur. The acetabulum is then prepared (reamed) and an acetabular cup with a liner inserted therein for engaging the femoral component.

Previously known techniques and apparatus for performing hip replacements require substantial soft tissue dissection and dislocation of the hip joint to obtain/maintain adequate exposure to ream the acetabulum. Preparation of the femur is typically performed, with reference to the femoral neck and head, in the direction from proximal to distal (cephalad-to-caudal/head-to-tail), such that the femoral neck can be directly visualized in all of these procedures. By way of example, preparation of the femur in these procedures can involve: dissection and retraction of the soft tissues to expose the femoral neck; then cutting the femoral neck with a saw under visual supervision; pushing reamers, or hitting bone broaches, down into the femoral canal in a direction from proximal to distal. Preparation of the acetabulum is typically performed after moving (retracting) the femur out of the way, and under direct vision through the incision, by reaming the surface through the incision.

Certain prior art techniques seek to minimise femoral dislocation utilising nonlinear reamers which may, for example, comprise a distal universal joint to ream at an angle. However, it is difficult to provide sufficient force with such apparatus or to obtain correct alignment.

As such, the present invention reams the acetabulum using a reaming rod passing lateromedially (i.e. lateral to medial) through the femoral neck.

However, we found that a significant problem or deficiency with such is that the reaming rod would typically require a diameter of 10-15 mm to have sufficient strength to impart the requisite drive and rotation for reaming the acetabulum.

We found that this particular diameter could weaken or inadvertently fracture the femur. Furthermore, even slight movement of the surgeon's and/or patients body could further undesirably stress the femoral bone.

As such, the present invention is characterised in the utilisation of an intramedullary broach or similar shaped device which comprises a superior transverse bore through which smaller diameter rods may be inserted for reaming, impaction and the like. Stress may be taken from the smaller diameter rods utilising an orthogonal distal drive arm of an arthroplasty jig which is inserted between the femur and the acetabulum via incision.

As such, the present methodology and apparatus allows utilisation of a much smaller diameter reaming rod being less than approximately 10 mm in diameter. In an embodiment, the reaming rod comprises a diameter of approximately 4.5-5.5 mm mm thereby better preserving the integrity of the bone of the femur and minimizing the risk of fracture.

Furthermore, the present intramedullary broach may increase acetabular component placement accuracy by making reference to the non-variant intramedullary axis of the femur and the non-variant bore axis of the broach.

In embodiments, a drill guide wire may initially be accurately guided through the transverse bore at an appropriate angle which may use angle guidance inserts located within the transverse bore. The drill guide wire may be followed utilising a cannulated overdrill for the making of a femoral neck passage of less than 10 mm in diameter, preferably less than about 5-6 mm in diameter (being much smaller than the diameters of the prior art arrangements).

For reaming, reaming rod may insert through the prepared femoral neck passage to rotate a cutting head located at a distal end thereof to ream the acetabulum. The reaming rod may be cannulated to follow the guide wire.

An orthogonal distal arm of an arthroplasty jig may locate behind the cutting head (including by way of bearing and adapter plates) to operatively press the cutting head into the acetabulum and bear most of the driving force such that little or no driving force is taken by the reaming rod thereby allowing for the reduced diameter thereof.

Cup impaction may be similarly performed wherein an impactor rod is inserted through the broach for impacting an implant wherein, again, the arthroplasty jig takes most or all the impaction force.

Embodiments may comprise an insertable guide plugs which locate within the broach bore for angle adjustment. In further embodiments may comprise adjustable apparatus for trial reduction.

Apparatus is also provided herein for the present techniques which may include an arthroplasty jig which is configured for both distraction and driving. Specifically, the arthroplasty jig may comprise a framework having a spine and a proximal orthogonal handle. The spine may support a distal orthogonal pelvic distraction arm and an opposing orthogonal femoral distraction arm that moves along the spine with respect to the pelvic distraction arm.

As such, the femoral distraction arm may be moved apart from the pelvic distraction arm to distract the femur away from the pelvis and conversely, moved towards the pelvic distraction arm during reaming and impaction. The pelvic distraction arm may be disengageable orthogonally away from the acetabulum during reaming and impaction. The pelvic distraction arm may further comprise an acetabulum rim or pelvic plate engagement for fastening to the pelvis. Furthermore, the femoral distraction arm may comprise a shaft accommodation at a distal end thereof for engaging the reaming or impaction shaft therethrough.

The arthroplasty jig may further comprise a drive arm which may be furthermore orthogonally transitionable between engaged and disengage positions. When the joint is distracted, the drive arm is disengaged out of the way for attachment of various componentry to the distal ends of the various rods and, conversely, when engaged, the distal end of the drive arm locates behind and operably presses against the cutting head or compactor adapter to impart force thereon.

The apparatus may further comprise a reduction device for guiding an implant head into a prepared liner socket. The reduction device may comprise a fork comprising tines which avoid the liner entrance and engage either a superior edge of the implant or the pelvic foramen.

The reduction device may further comprise a bearer that is offsettable with respect to the fork to push the implant head towards the socket aperture.

Furthermore, certain present embodiments may counter drive rod rotation eccentricities that could fracture the femoral neck.

According to one aspect, there is provided a method for performing hip arthroplasty involving a femur having a femoral shaft, neck and head and an adjacent pelvis having an acetabulum formed thereon, the method comprising: intramedullary insertion of an elongate femoral broach into the shaft, the broach comprising a superior lateromedial transverse bore; locating a reaming rod through the transverse bore and femoral neck; coupling a cutting head to a distal end of the reaming rod via an incision; and rotating the cutting head using the reaming rod to ream the acetabulum.

US 2006/0200160 A1 to Border et al. teaches an internal fixation assembly and associated method which includes an elongated intramedullary implant for a long bone, the intramedullary implant defining a transverse bore having an inlet opening and an outlet opening, and a strength-enhancing lip surrounding at least one of the inlet and outlet openings. The lip includes a continuous curved surface having a continuous slope.

However, Border fails to teach or suggest locating a reaming rod through a transverse bore of a femoral broach and further fails to disclose the steps of coupling a cutting head to a driveshaft or pressing a drive arm of an arthroplasty jig behind a cutting head.

The method may further comprise inserting an orthogonal drive arm of an arthroplasty jig to locate and operatively press behind the cutting head and driving the cutting head using the drive arm a further feature of which Border is silent.

Locating the reaming rod may comprise: drilling of a guide wire through the transverse bore and femoral neck and head; following the drill guide wire with a cannulated overdrill to form a femoral neck passage; removing the cannulated overdrill; and following the drill guide wire with the reaming rod.

The femoral neck passage may comprise a diameter of less than 10 mm. The femoral neck passage may comprise a diameter of between 3 and 8 mm. The femoral neck passage may comprise a diameter of less than 6 mm. The femoral neck passage may comprise a diameter of between 4 mm and 6 mm.

The method may further comprise inserting the femoral broach utilising a femoral handle.

The method may further comprise controlling the insertion depth of the femoral broach utilising an insertion depth referencer on the femoral handle.

The insertion depth referencer may comprise a depth referencing pin referencing the femur, the depth referencing pin being orthogonal with an intramedullary axis of the femur.

The depth referencing pin may reference the greater trochanter of the femur.

The method may further comprise attaching a referencing guidance jig to the femoral handle and wherein the referencing guidance jig may comprise a position regulator and wherein the method may comprise guiding the guide wire lateromedially towards the bore through an aperture of the position regulator.

The position regulator may comprise a plurality of apertures and wherein the method may further comprise selecting one of the apertures according to a desirous insertion angle.

The method may further comprise drilling the guide wire mediolaterally through the bore utilising a curved guidance tube.

The bore may have a cross-section parallel an elongate axis of the broach and wherein the cross-section is wider along the elongate axis.

The bore may taper latermedially.

The bore may define a lateral entrance and a medial exit and wherein the method may further comprise placing a guide wire insert having a guide bore into the bore exit and guiding the drilling guide wire through the guide bore.

The method may further comprise selecting the guide wire insert from a selection of guide wire according to a guide bore angle.

The method may further comprise removing the cutting head and attaching an implant to a distal end of an impactor rod located through the bore via an implant adapter and striking an orthogonal proximal handle of the arthroplasty jig to drive the implant into the acetabulum via the drive arm.

The method may further comprise screwing fixation screws through the implant utilising a screw driver inserted via the bore.

A distal end of the screwdriver may be flexible.

The method may comprise manipulating the femur to position the distal end of the screwdriver.

The method may further comprise trial reduction comprising insertion of a liner within the implant and location of trial inserts of differing lengths along a trial reduction rod between the broach and a trial head located within the implant.

The method may further comprise trial reduction comprising insertion of a liner within the implant and insertion of a screw rod screwably engaged to the broach, the screw rod having a trial head at a distal end thereof and rotating the screw rod with respect to the broach to adjust the length and offset of the trial head away from the broach.

The method may further comprise removal of the broach and the intramedullary insertion of an implant.

The method may further comprise engaging diverging tines of a fork of a reduction device about an entrance of a liner inserted within the implant and locating a head of the implant against a stem of the fork and adjusting a bearer of the device with respect to the fork to push the head towards the liner entrance.

Distal ends of the diverging tines may engage at least one of an inferior edge of the implant and the pelvic foramen.

The arthroplasty jig may further comprise a femoral distraction arm and a pelvic distraction arm and wherein the method may further comprise distracting the femur away from the pelvis by offsetting the femoral distraction arm away from the pelvic distraction arm.

The orthogonal drive arm may be orthogonally transitionable between disengaged and engaged positions and wherein the method may further comprise engaging the orthogonal drive arm behind the cutting head and around the reaming rod and disengaging a locking mechanism to relax the femoral distraction arm towards the pelvic distraction arm.

The method may further comprise adjusting an orientation of the femoral shaft to adjust a reaming angle of the reaming rod.

The method may further comprise orientating the femoral shaft parallel with the ground.

According to another aspect, there is provided femoral broach apparatus comprising a femoral broach comprising an elongate body for intramedullary insertion and a superior transverse bore therethrough.

The bore may have a cross-section parallel an elongate axis of the elongate body which is wider along the elongate axis so as to allow aiming of a reaming rod inserted therethrough in use. In this way, the angle of the reaming rod may be adjusted with respect to the elongate body to adjust the aim of the rod through the femoral neck and head.

The cross-section of the transverse bore may be ovular.

The bore may taper lateromedially.

The transverse bore may define an entrance and exit and further comprising at least one guide wire insert for location within the exit, the at least one guide wire insert comprising a guide bore.

The at least one guide wire insert may comprise a plurality of guide wire inserts each having transverse bores of differing angles.

According to another aspect, there is provided an arthroplasty jig comprising a spine, an orthogonal proximal handle, an orthogonal pelvic distraction arm and an orthogonal femoral distraction arm, the femoral distraction arm offsettable from the pelvic distraction arm along the spine.

A medial face of a distal end of the pelvic distraction arm may comprise an acetabulum rim engagement.

A distal end of the pelvic distraction arm may comprise a pelvic fixation plate.

The pelvic distraction arm may be orthogonally offsettable between engaged and disengaged positions.

The arthroplasty jig may further comprise an orthogonal drive arm located between the femoral distraction arm and the pelvic distraction arm.

The orthogonal drive arm may be orthogonally offsettable between engaged and disengaged positions.

A distal end of the orthogonal drive arm may comprise a shaft accommodation.

A distal end of the femoral distraction arm may comprise a shaft accommodation.

A distal end of the proximal handle may comprise a shaft accommodation.

According to another aspect, there is provided a reduction device comprising a fork and a relatively offsettable bearer, the fork comprising a stem diverging into two tines.

The bearer may be screwably offsettablly engaged to the fork.

Distal ends of the times comprise hooks for at least one of implant rim or pelvic foramen engagement.

Other aspects of the invention are also disclosed.

BRIEF DESCRIPTION OF THE DRAWINGS

Notwithstanding any other forms which may fall within the scope of the present invention, preferred embodiments of the disclosure will now be described, by way of example only, with reference to the accompanying drawings in which:

FIGS. 13-14 show implant cup impaction using the arthroplasty jig in accordance with an embodiment;

FIG. 32 illustrates the broach handle engaging the femoral broach in accordance with an embodiment;

DESCRIPTION OF EMBODIMENTS

Figure 1:
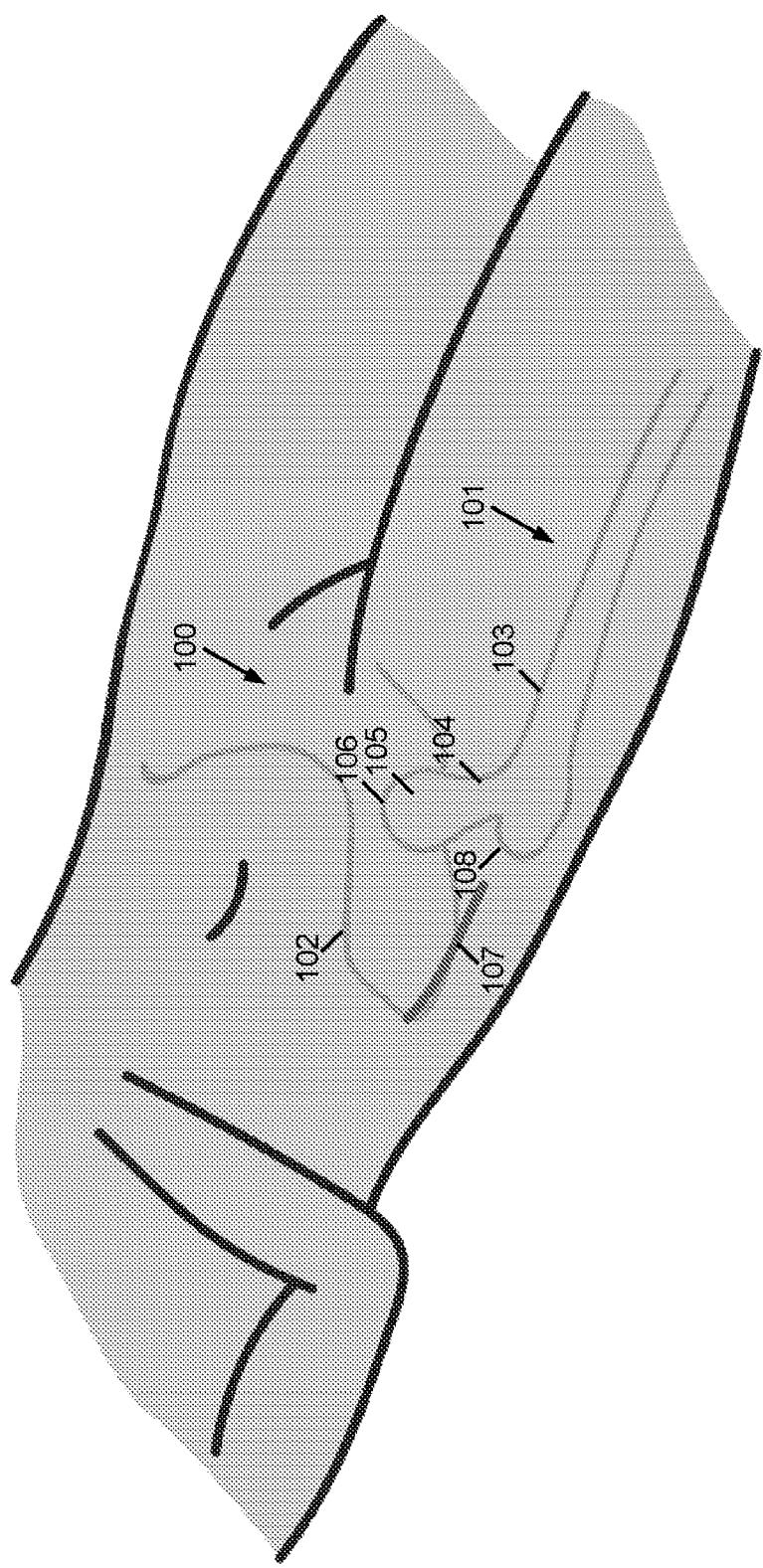
FIG. 1 shows a hip joint for reference herein.

FIGS. 1-25 illustrate hip joint 100 arthroplasty techniques. As can be seen from FIG. 1, the hip joint 100 comprises a femur 101 having a femoral shaft 103, neck 104, head 105 and greater trochanter 108. The femur 101 locates adjacent a pelvis 102 having an acetabulum 106 formed therein.

The hip joint 100 may be accessed via a superior incision 107 in the general location shown in FIG. 1.

Orientation will be described hereafter with reference to superior being towards the head and inferior being towards the feet of the patient. Furthermore, the lateral and derivatives thereof refer to out away from the side of the body in the dorsal planes and medial and derivatives thereof in towards the side of the body in this plane. Lateromedially refers to in a direction from lateral to medial and mediolaterally refers to the opposite direction.

Figure 2:
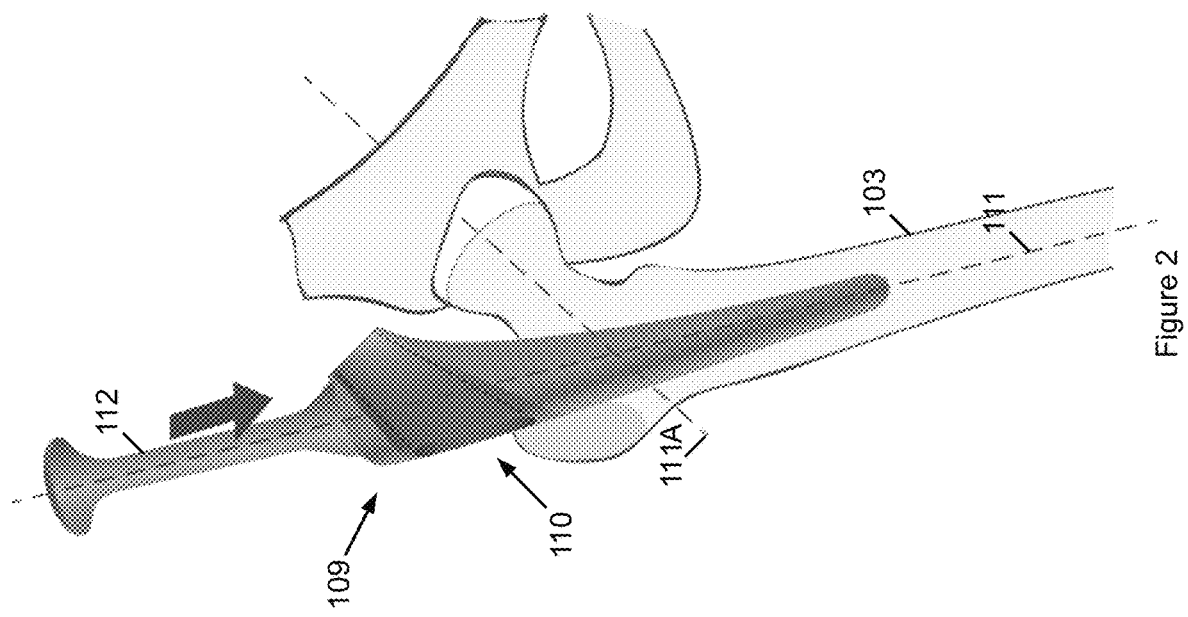
FIG. 2 shows the insertion of an intramedullary broach comprising a transverse bore into a superior end of a femur utilising a broach handle in accordance with an embodiment.

Referring to FIG. 2, the method comprises the insertion of an elongate femoral broach 109 into the medullary cavity of the shaft 103 of the femur 101 along the intramedullary axis 111.

Typically, the superior end of the femur 101 would be accessed via the superior incision 107. Once accessed, the piriform fossa of the femur 101 may be drilled to make allowance for the broach 109. A series of broaches 109 of increasing size may be trialled to determine the appropriate sizing thereof.

A detachable broach handle 112 may selectively engage the superior end of the broach 109. The superior end of the broach handle 112 may be struck with a mallet to drive the broach 109 into the intramedullary canal.

The femoral broach 109 comprises a superior mediolateral transverse guidance bore 110 generally in alignment with a femoral neck axis 111A. The transverse bore 110 will be described as having a lateral entrance and a medial exit. The exterior surface of the femoral broach 109 adjacent the guidance bore may be smooth to allow more material in the broach in this area to maximise strength of the broach.

Figure 3:
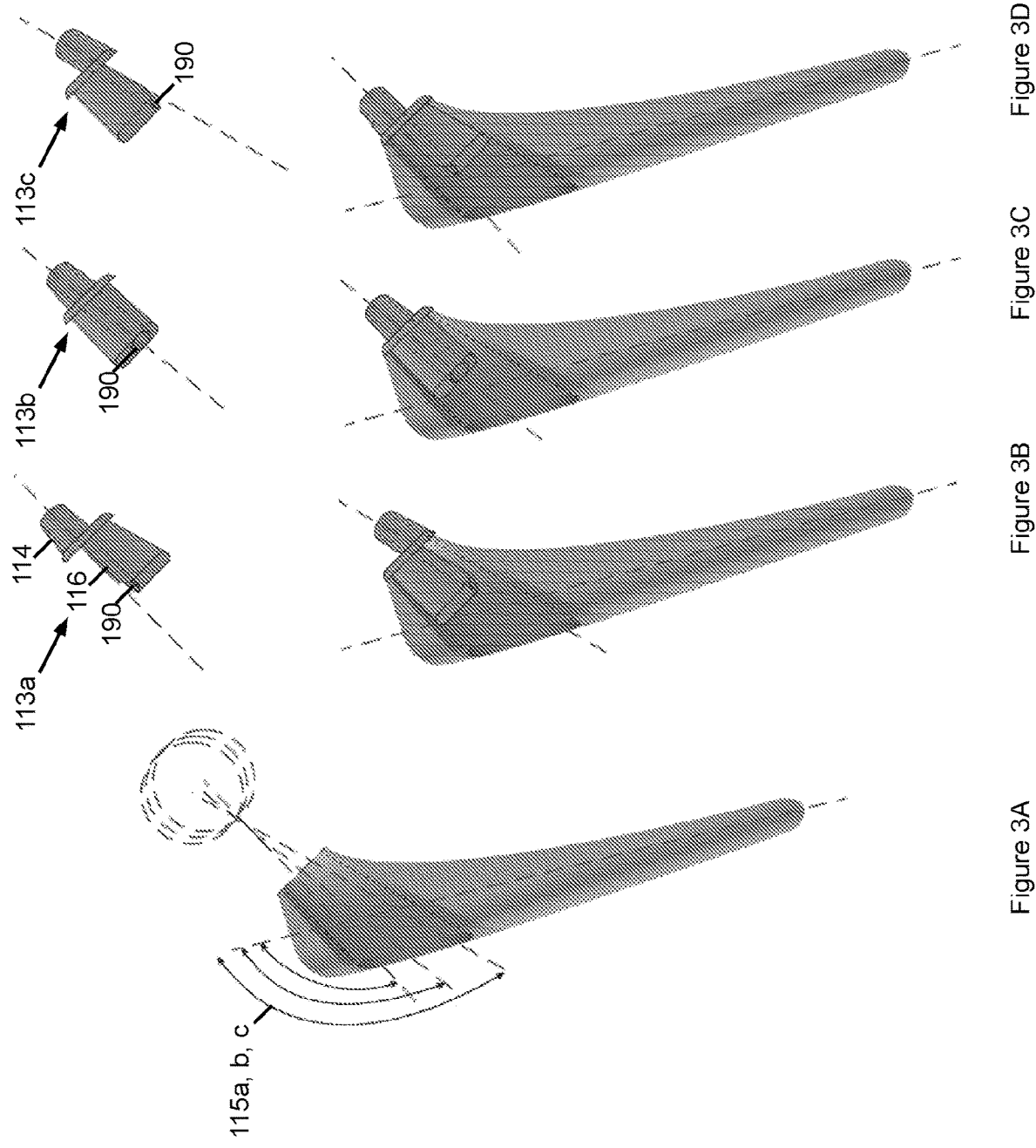
FIG. 3 illustrates the utilisation of differing bore inserts for approach angle guidance and offset adjustment in accordance with an embodiment.

FIG. 3 shows that the bore 110 can be wider along and elongate axis of the broach 109 (such as by having an ovular cross-section in one embodiment) for variance of the implant angle 115 for different types of implants. Furthermore, the bore 110 can taper lateromedially. The broach 109 in other embodiments may have a cylindrical bore if angle adjustment is not required.

In embodiments, the apparatus may comprise one or more insertable guide plugs 113 which have guidance bores 190 therethrough. The insertable guide plugs 113 may comprise a lateral insertion portion 116 that is secured within the bore exit and a medial nib 114 that stands proud from the bore 110.

Furthermore, differing insertion guides 113 having differing guidance bore 190 angles may be utilised to vary the insertion angle 115 to mimic the angle of the chosen implant component. In embodiments, the extent of the nib 114 may be used to adjust femoral offset.

Specifically, FIGS. 3B-3C show three types of insertion guide 113 of increasing guidance bore 190 angles. An implant may comprise a plurality of insertion guides 113 for trialling of differing angles and offsets therefore.

Once the femoral broach 109 is located, the femoral neck 104 may be cut to remove the head 105.

A guide wire 123 may then be drilled through the broach 109.

Figure 4:
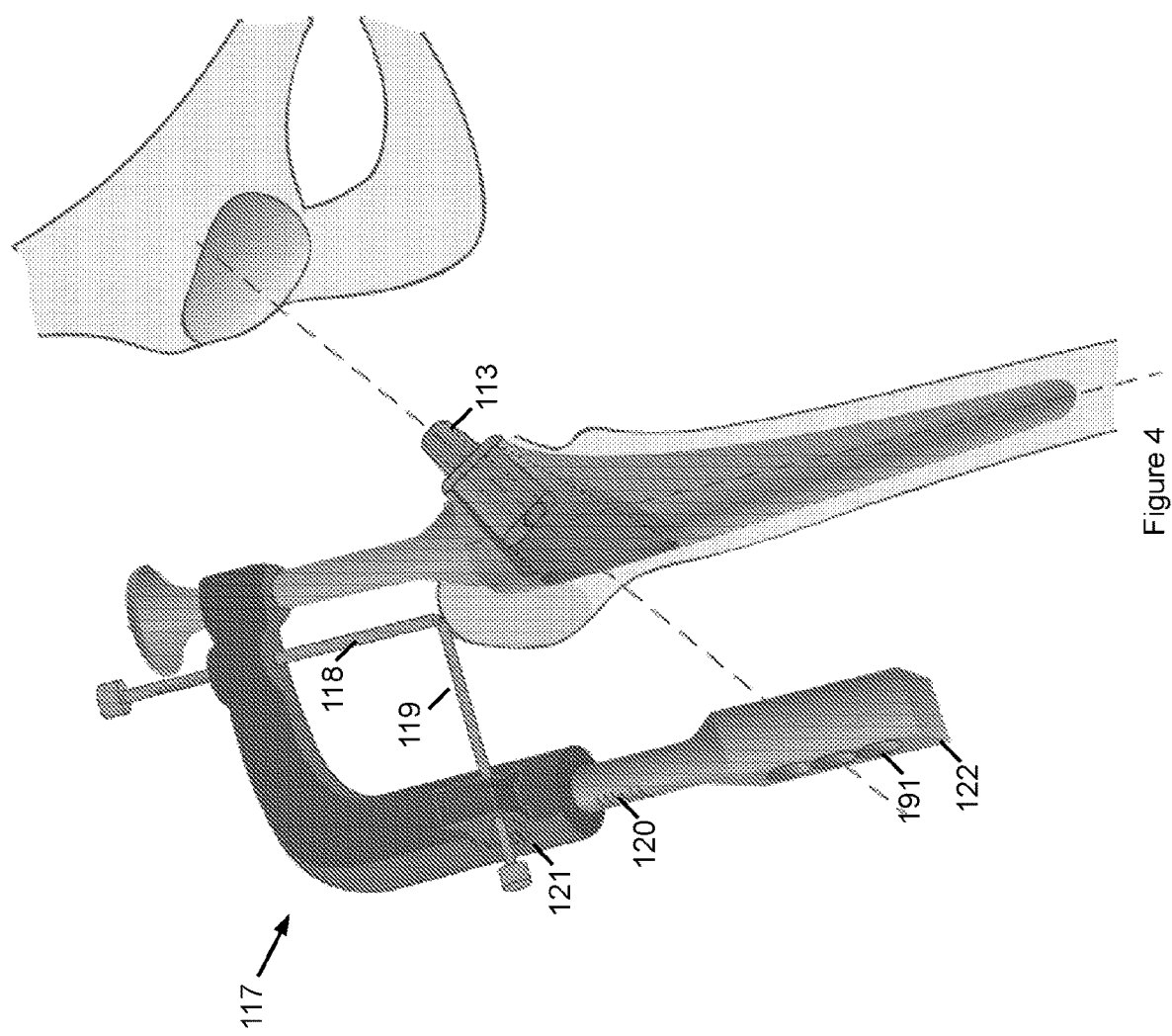
FIGS. 4-6 shows the lateromedial insertion of a drill guide wire through the broach to the acetabulum including utilising a guidance jig in accordance with an embodiment.
Figure 5:
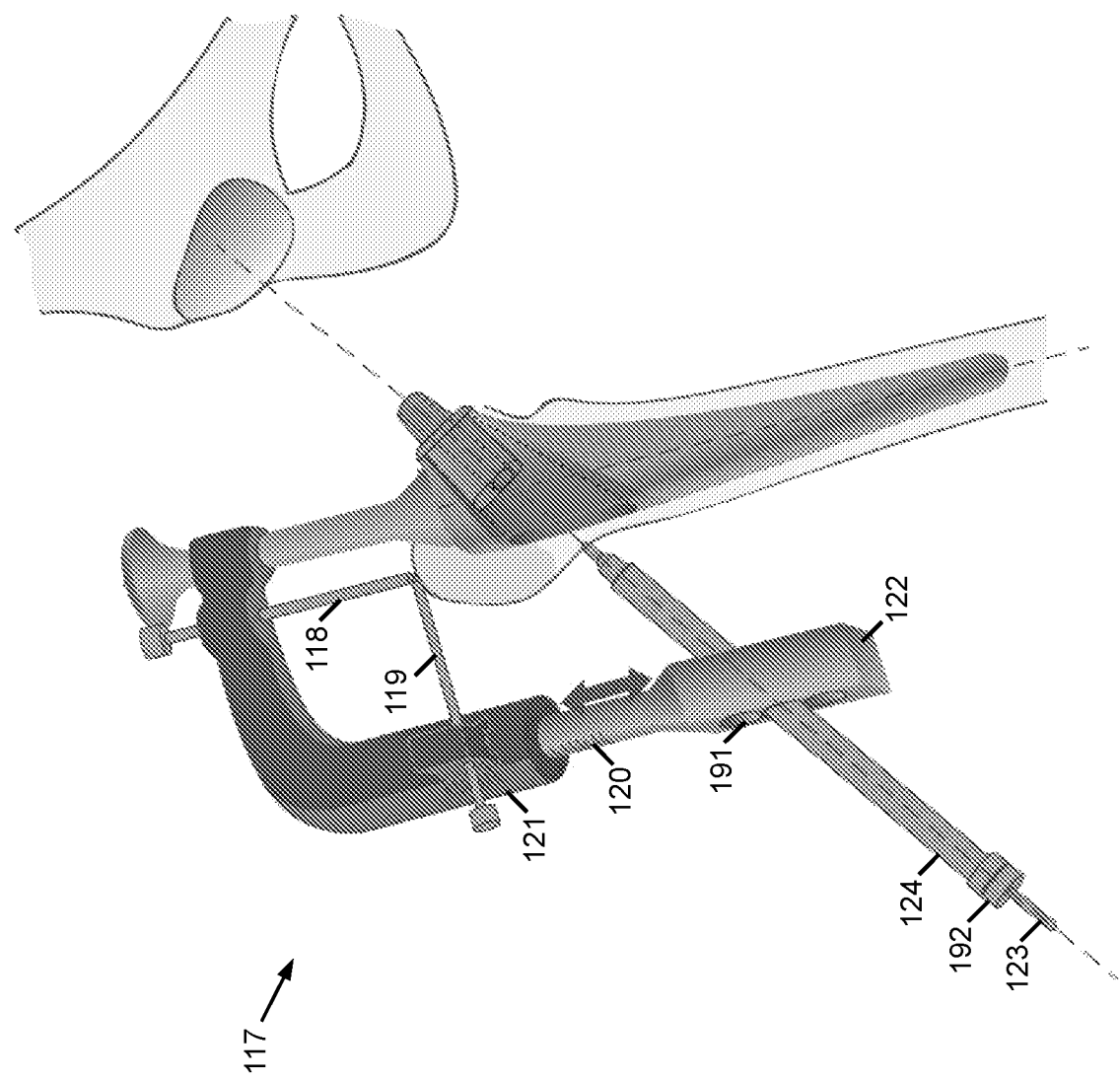
Figure 6:
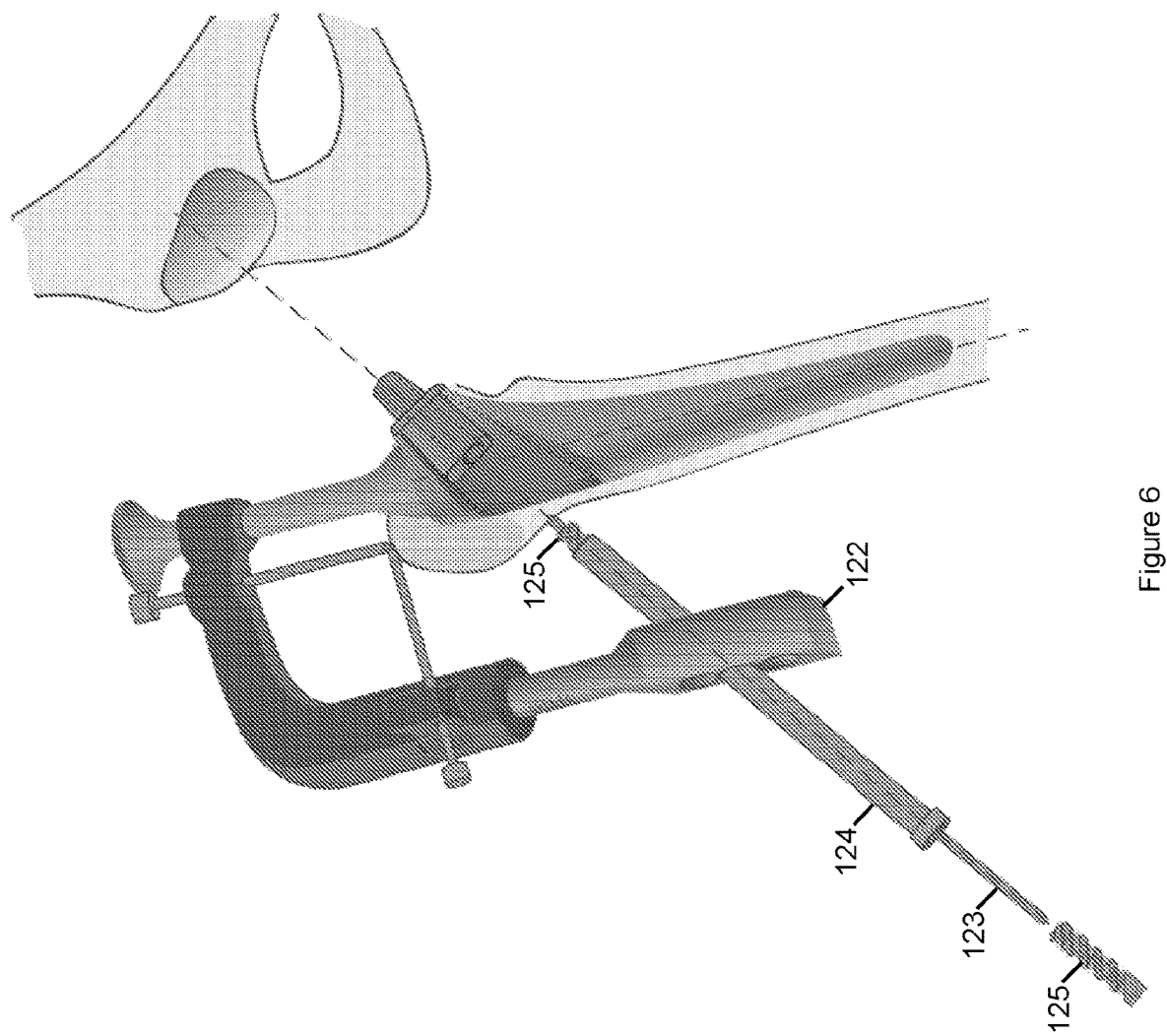

FIGS. 4-6 show the lateromedial drilling of the guide wire 123 using a guidance jig 117 which may attach to the broach handle 112.

The guidance jig 117 may reference the greater trochanter 108 with an adjustable and demarcated depth reference pin 118 in line with the intramedullary axis 111 and/or an orthogonal lateral offset reference pin 119. The orthogonal reference pin 119 may be controlled with an offset adjustment mechanism 121.

The guidance jig 117 may comprise an offset adjustable position regulator 122 and associated offset demarcations 120.

Once the depth of the broach 109 has been set utilising reference pins 118, 119, the position of the adjustable position regulator 122 is adjusted according to the desirous insertion angle.

The adjustable position regulator 122 may comprise a plurality of apertures 123 of differing angles aiming towards the inserts 113 within the bore 110. In the embodiment shown, the adjustable position regulator 122 may comprise three apertures 191 corresponding to each of the inserts 113.

As is shown in FIG. 5, once the adjustable position regulator 122 has been set correctly, the guide wire 123 can be drilled through the bore 110 via a sleeve 124 located within the appropriate aperture 123.

A diameter narrowing cannulated insert 192 may locate within the sleeve 124 for snugly engaging the guide wire 123.

The distal end of the guide wire 123 passes through the bore 110 and the guidance insert 113 towards the acetabulum 106.

Thereafter, once the guide wire 123 is set at the correct angle, as can be seen from FIG. 6, a cannulated overdrill 125 may follow the guide wire 123 within the sleeve 124 to form femoral neck passage of approximately 5 mm diameter (but potentially from approximately 3 mm-8 mm) through the bore 110.

Embodiments of the procedure may be performed without the use of the guide wire 123, albeit with difficulty.

Figure 7:
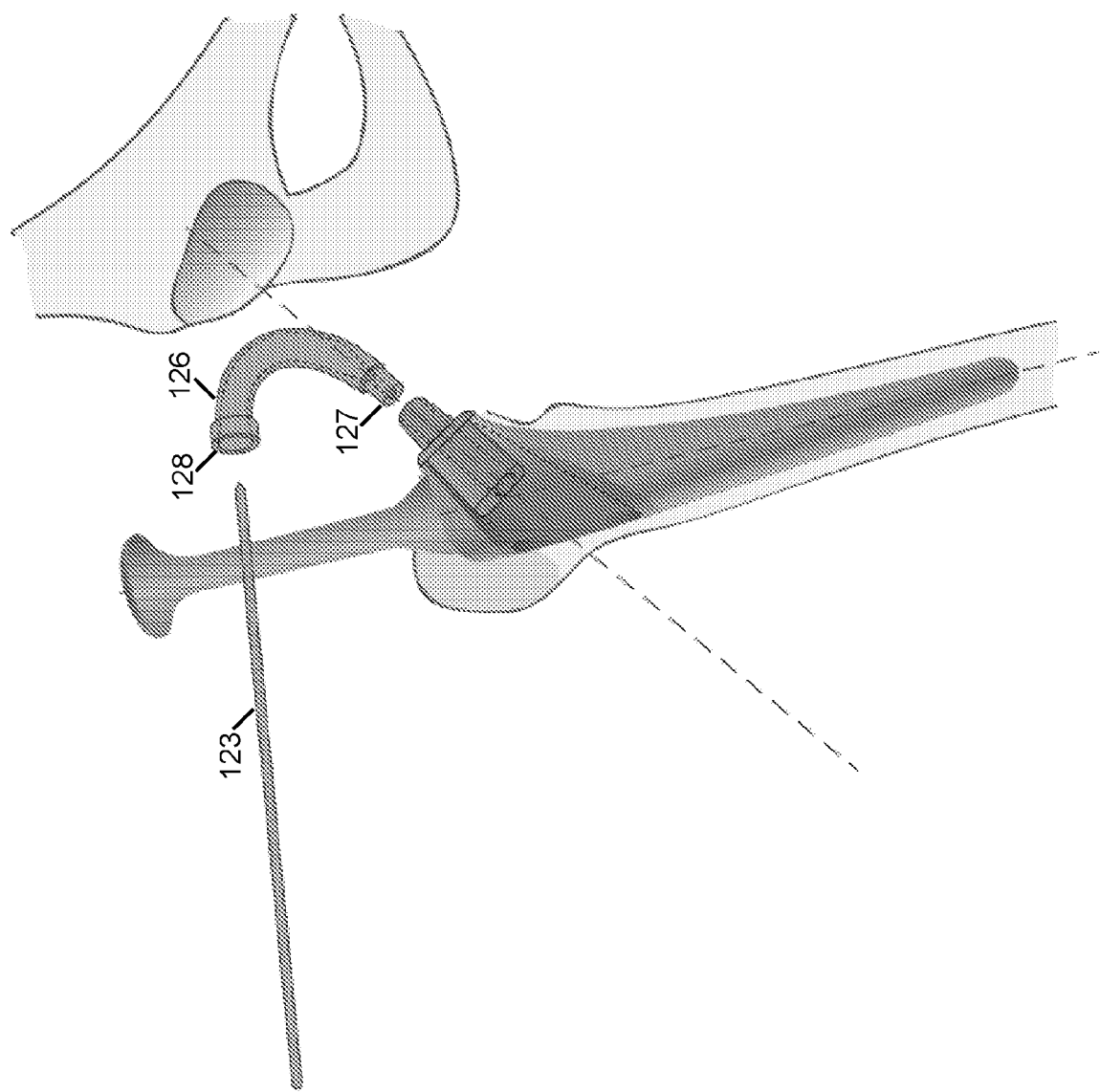
FIGS. 7-9 shows the mediolateral insertion of a drill guide wire using a curved guidance tube through the broach in accordance with an embodiment.
Figure 8:
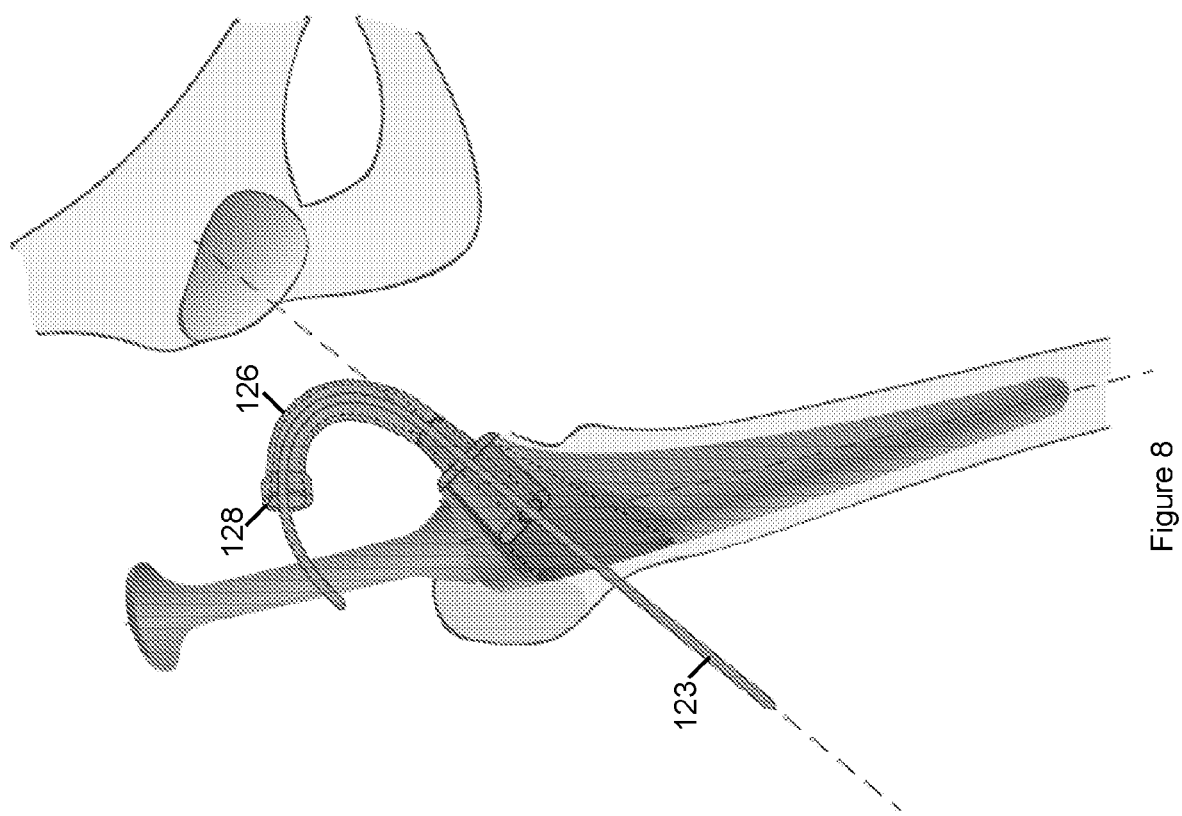
Figure 9:
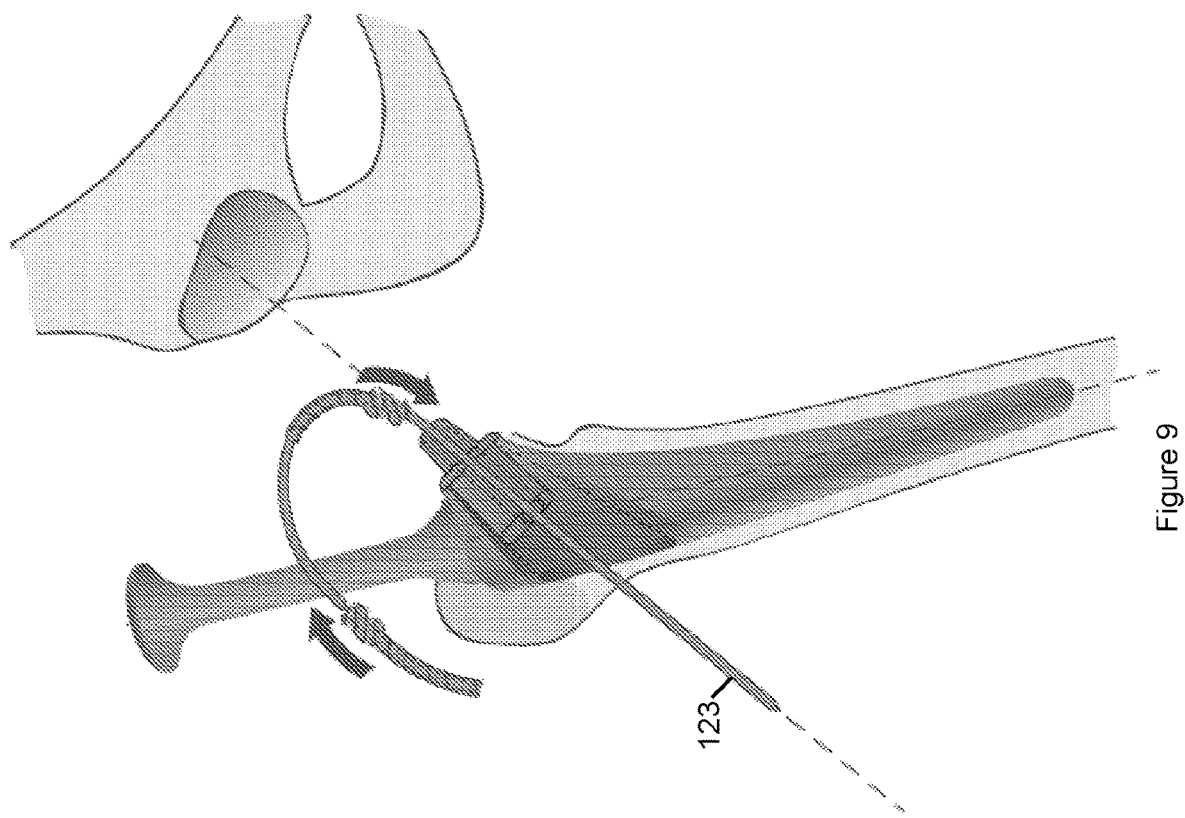

FIGS. 7-9 alternatively show the mediolateral drilling of the guide wire 123 using a curved guide tube 126 which may be inserted between the femur 101 and the acetabulum 106 via the incision 107 or another incision.

The curved guide tube 126 comprises an entrance 128 which may be widened to receive the drill guide wire 123. The curved guide wire 126 further comprises an exit 127 which may narrow to interlock coaxially with the nib 114 of the insert 113 and to snugly rotatably engaged the guide wire 123 therethrough.

FIG. 8 shows the flexible guide wire 123 being guided around the guide tube 126 through the insert 113 and the bore 110 so as to exit laterally via the thigh.

In embodiments, as opposed to utilising a curved guide tube 126, the straight drill may be used mediolaterally with or without a guide wire 123.

FIG. 9 shows a flexible cannulated overdrill 125 following the drill guide wire 123 to form the femoral neck passage of approximately 5 mm in diameter.

Figure 10:
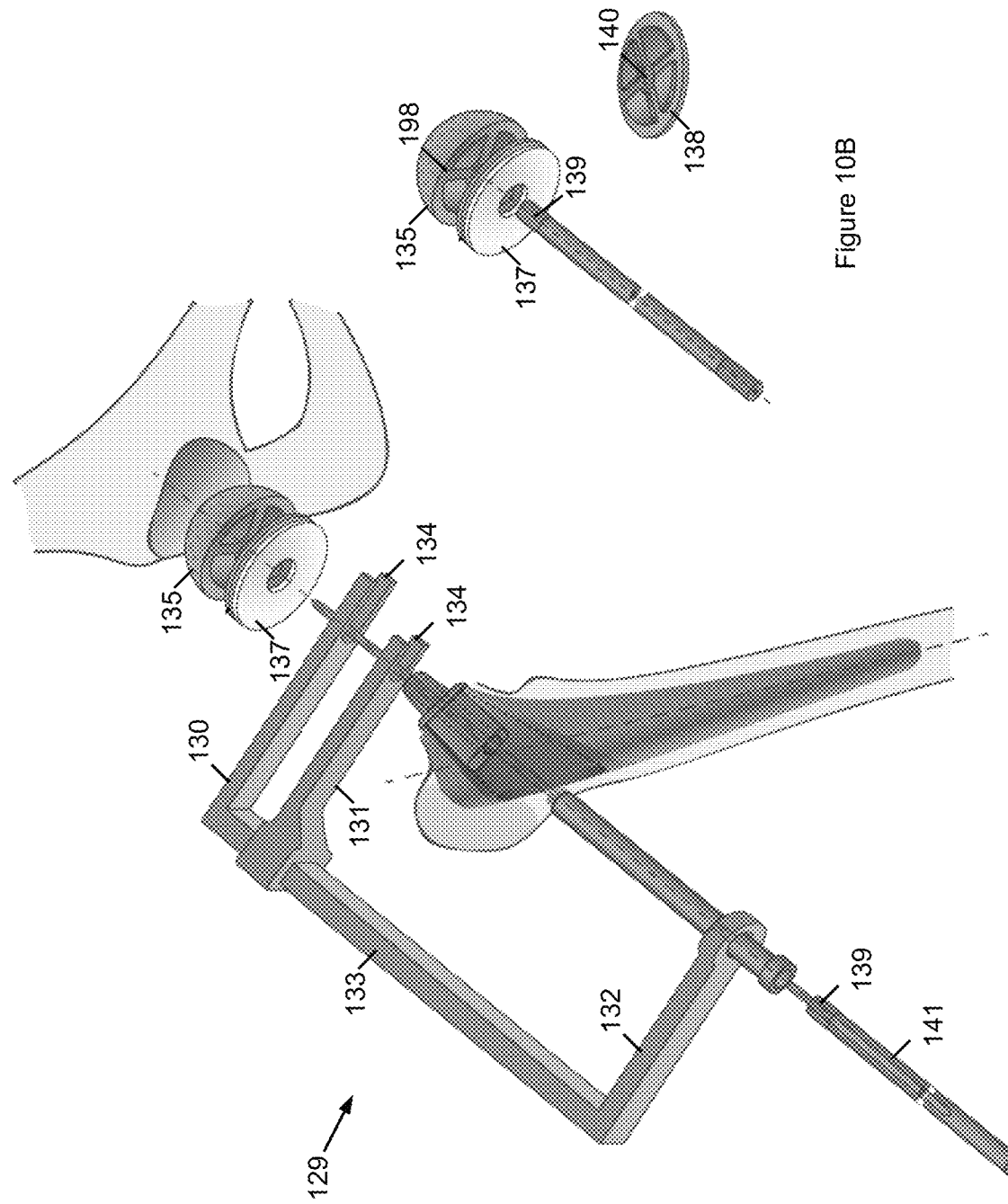
FIGS. 10-12 show the reaming of the acetabulum utilising an arthroplasty jig in accordance with an embodiment.

Having formed the femoral neck passage, FIG. 10 shows the utilisation of an arthroplasty jig 129 for reaming the acetabulum 106 in an embodiment.

The arthroplasty jig 129 comprises a rigid framework having a spine 133 and an orthogonal drive arm 130. The jig 129 may also have an offset arm 131 and proximal handle 132. The orthogonal drive arm 130 and offset arm 131 may insert a via the incision 107 or another incision.

For reaming, there is shown a cannulated reaming rod 141 following the guide wire 123 through the broach 109 such that a cutting head 135 may be operably coupled to a distal end thereof. In embodiments, the reaming rod 141 may be uncannulated such as where the guide wire 123 is removed prior, or not used at all.

The distal ends of the drive arm 130 and the offset arm 131 may comprise notches 134, apertures or the like for accommodating the reaming rod 141 therethrough.

The proximal handle 132, femoral broach 109 and the drive arm 130 may co-operate to support the reaming rod 141 from three points therealong, increasing accuracy and preventing/reducing wobbling.

The cannulated reaming rod 141 may comprise a distal exterior connection 139 that engages a corresponding inner connection 140 of an adapter plate 138. The adapter plate 138 may comprise orthogonal channels which seat corresponding orthogonal rearward cross bars 198 (or other matching profile) of the cutting head 135. In alternative embodiments, the distal exterior connection 139 of the reaming rod 141 may engage a corresponding inner connection of the reamer 135 directly as opposed to via an adapter plate 138.

A freely rotating bearing plate 137 typically made of non-metal material (such as polyethylene) may locate behind the adapter plate 138 to minimise friction from the 134 and avoid metallosis.

The acetabulum 106 is then reamed utilising the cutting head 135. Reaming may comprise utilisation of a series of cutting heads 135 of increasing diameter.

Specifically, the reaming rod 141 may be rotated to correspondingly rotate the cutting head 135 whilst the drive arm 130 of the arthroplasty jig 129 operatively locates behind the bearing plate 137 to press the cutting head 135 into the acetabulum 106. The proximal handle 132 may be pressed to apply pressure on the bearing plate 137 via the drive arm 130.

Figure 11:
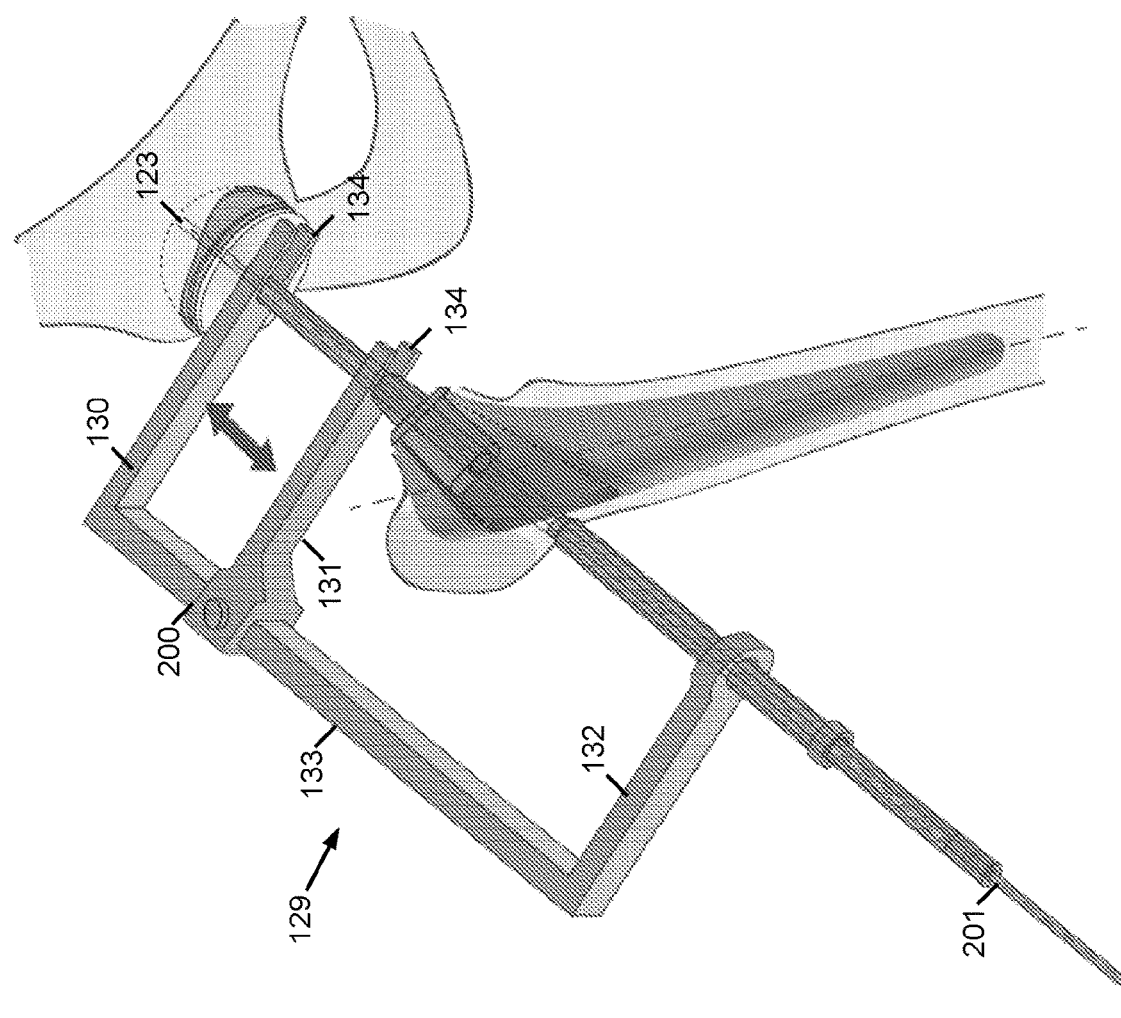

As is shown in FIG. 11, the offset arm 131 may slide along the spine 133 with respect to the drive arm 130 for gauging the distance between the broach 109 and the acetabulum 106. The spine 133 may comprising markings 200 therealong for reading the distance therefrom.

Figure 12:
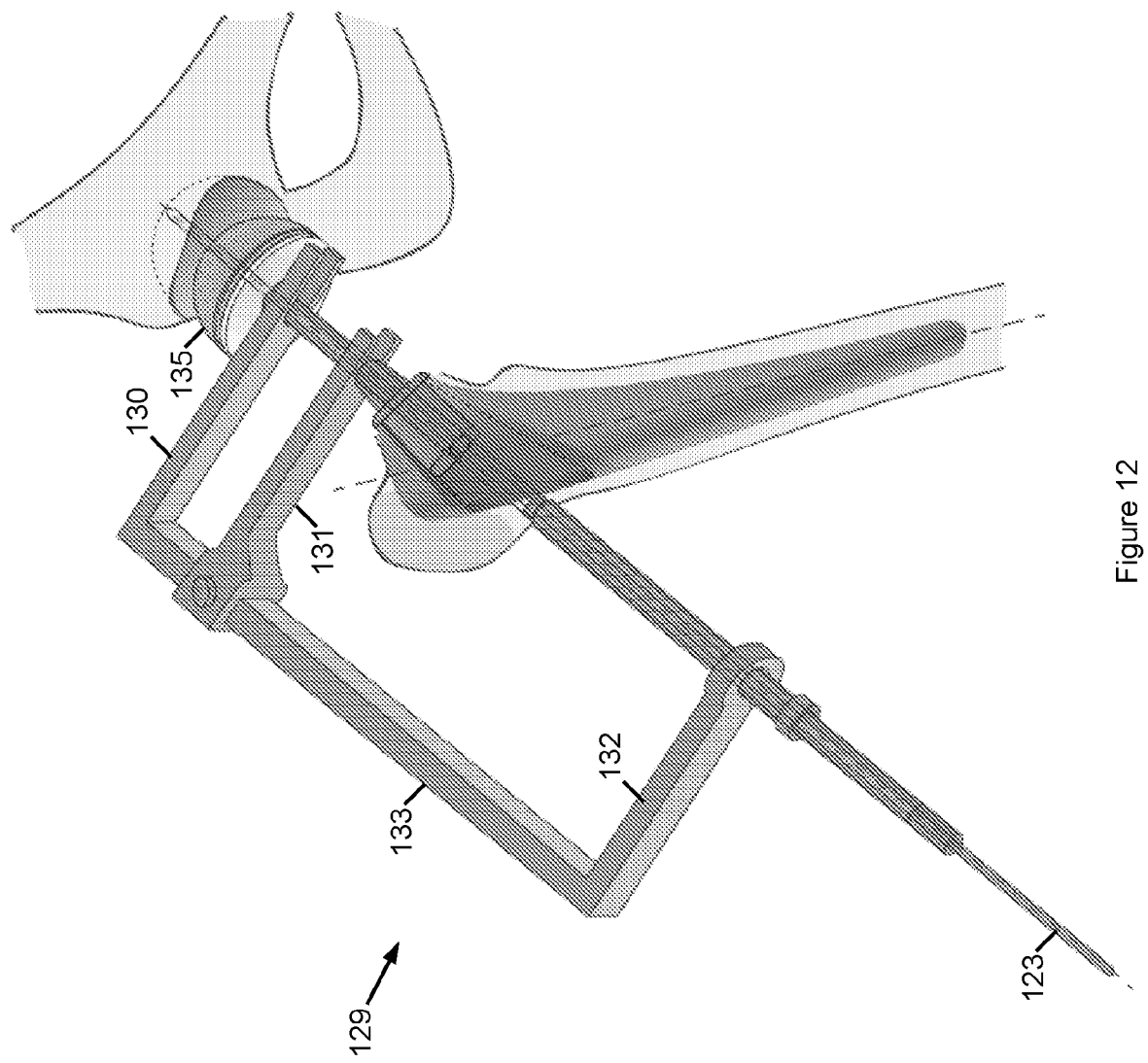

Conversely, as is shown in FIG. 12, locating the offset arm 131 towards the drive arm 130 may allow access for the visualisation and/or access to the cutting head 135.

As is shown in FIG. 11, the guide wire 123 may pass through an apex of the cutting head 135 to reference the floor of the acetabulum 106. As such, a differential scale 201 between the reaming rod 141 and the guide wire 123 may be referenced to ascertain the reaming depth.

In embodiments, the reaming rod 141 may be guided by the broach 109 with reference to the femur 103. As such, if the femur 103 is moved a number of degrees, the position of the acetabular reamer will similarly be adjusted by the same number of degrees. Furthermore, if the femur is parallel to the ground and the angle in the broach 109 is set then the position of the acetabulum can be accurately determined.

Figure 13:
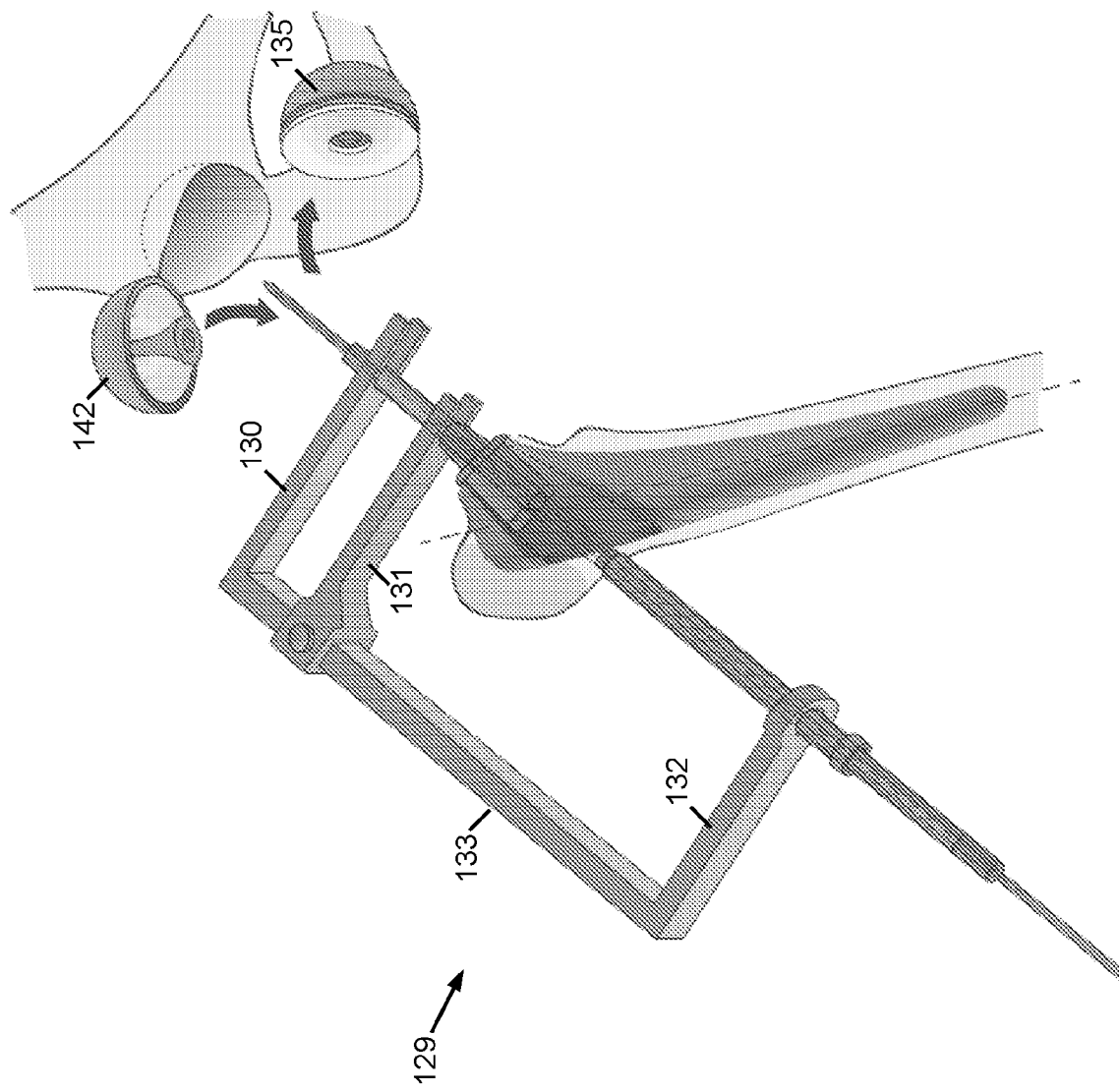

As is shown in FIG. 13, once the acetabulum 106 has been suitably reamed, the offset arm 131 is located close to the drive arm 130 to make allowance for the removal of the cutting head 135 and the substitution therewith with an acetabulum implant 142.

As is shown in FIG. 14, a conical adapter 143 may interface and inner apex of the implant 142 via confirming threading 144, 145 or other suitable meshing/engagement.

The reaming rod 141 may be removed and replaced with an impactor rod 172. Alternatively, the same reaming rod 141 may be utilised. A proximal end of the conical adapter 143 may define an engagement port 146 for engaging a distal end of the impactor rod 172.

An impactor rod outrigger 147 may be used to hold the proximal end of the impactor rod 172. The outrigger 147 may comprise a handle 173 and, in embodiments, a strike plate 148 which may be struck with a mallet, slapped with one's hand or the like.

The impactor rod 172 may similarly be cannulated for accommodating the guide wire 123 therethrough. Furthermore, the handle 173 may comprise a central bore through which the guide wire 123 passes. Similarly, a differential offset scale between the handle 173 and the guide wire 123 may indicate the depth of impaction of the implant 142.

The impactor rod 172 may primarily maintain the appropriate orientation of the implant 142 wherein the brunt of the impaction force may be bourne by the arthroplasty jig 129.

Having seated the implant 142, the conical adapter 143 may be removed from the implant 142, typically by unscrewing. Furthermore, the reaming rod 172 and reaming rod outrigger 147 may be removed.

Figure 15:
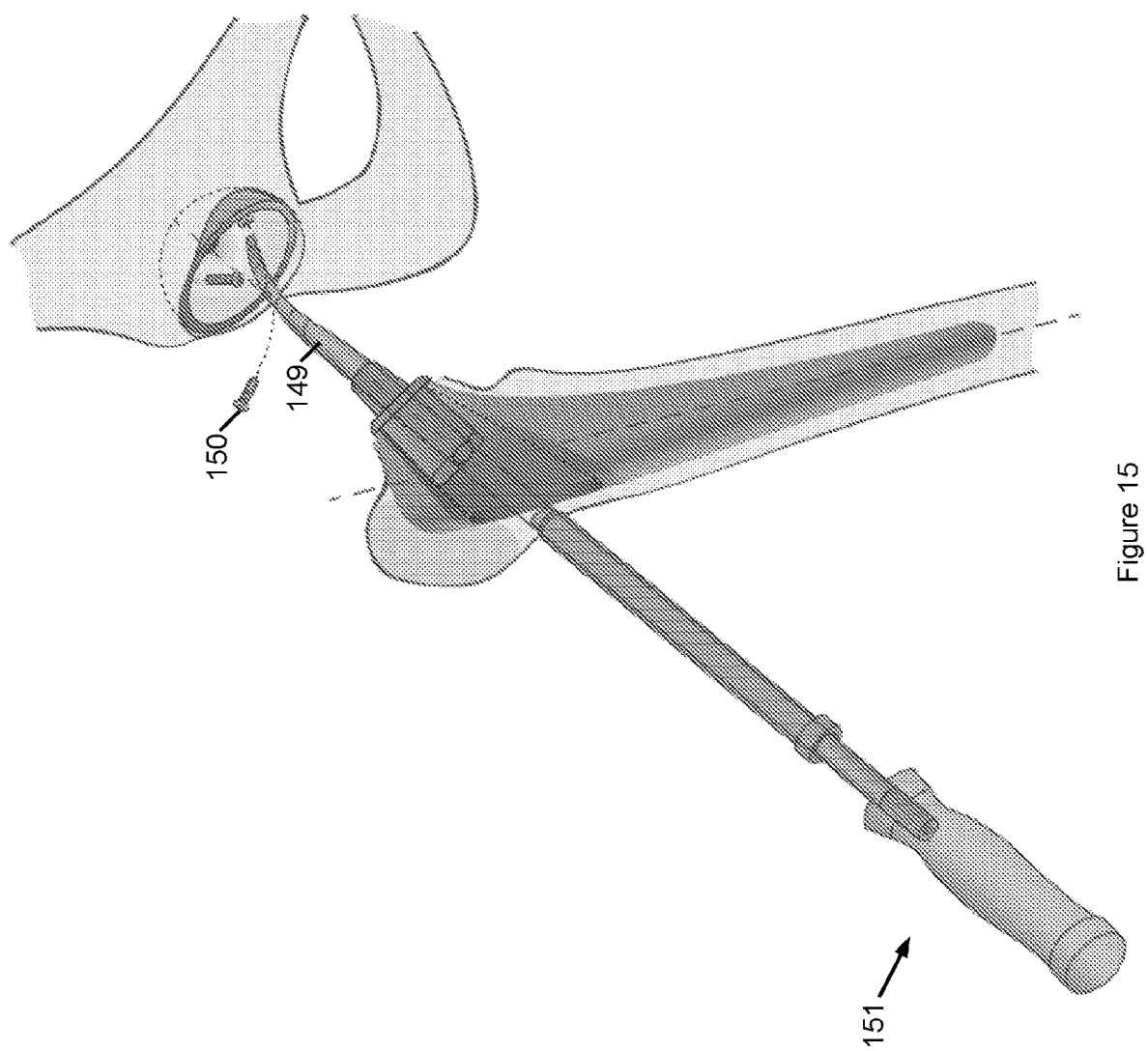
FIG. 15 shows the fixation of an implant cup using a screwdriver inserted through the femoral broach in accordance with an embodiment.

FIG. 15 then shows the utilisation of a screwdriver 151 having a screwdriver rod 149 used to fasten fixation screws 150 within the appropriate apertures of the implant 142 in an embodiment. The guide wire 123 may be removed for the insertion of the screwdriver 151.

In embodiments screwdriver rod 149 may be flexible so as to be able to be manually manipulated to the appropriate positioning. In embodiments, the leg of the patient may be positioned to orientate the screwdriver rod 149 appropriately.

Figure 16:
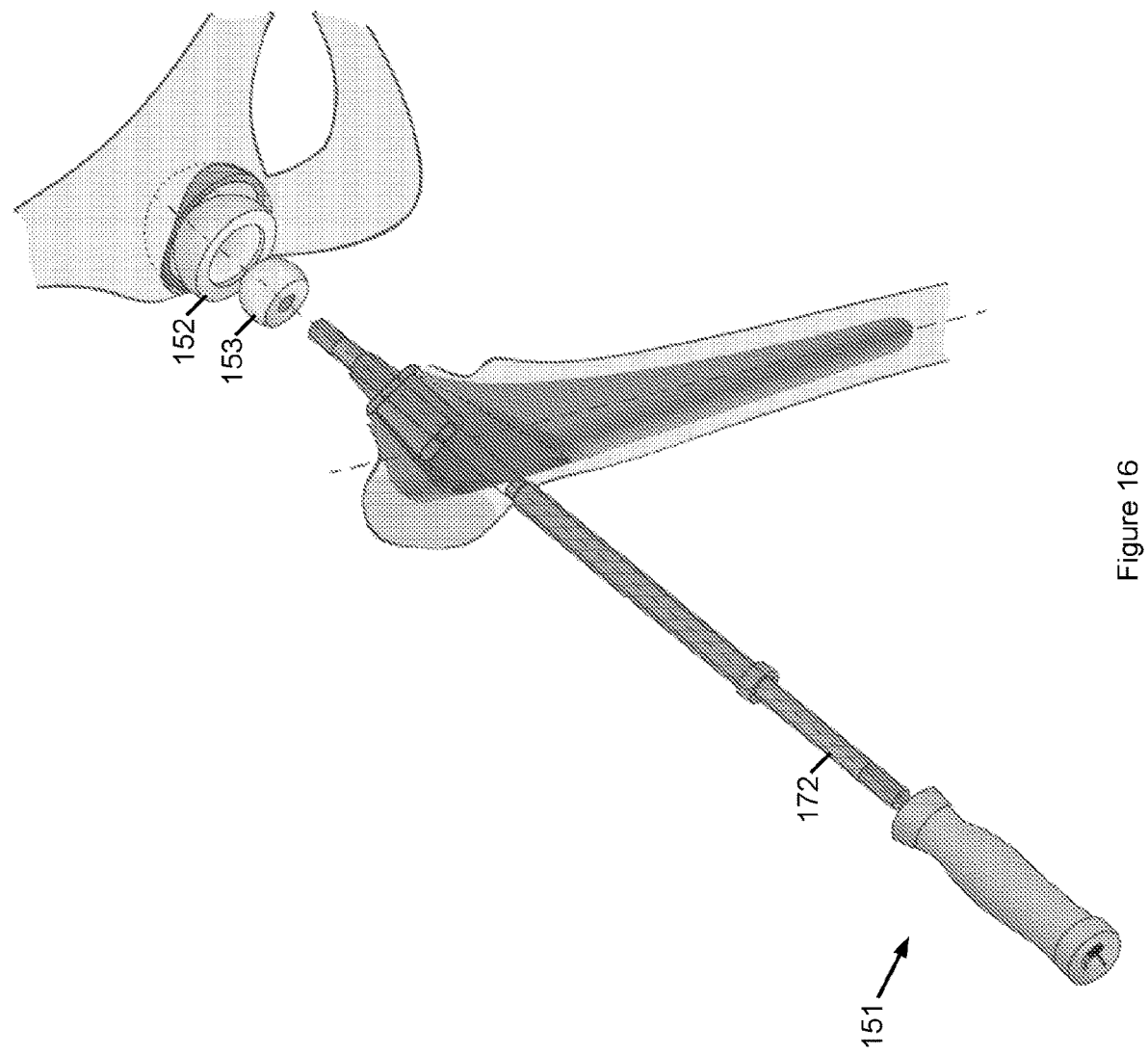
FIG. 16-17 illustrates liner insertion via the femoral broach in accordance with an embodiment.
Figure 17:
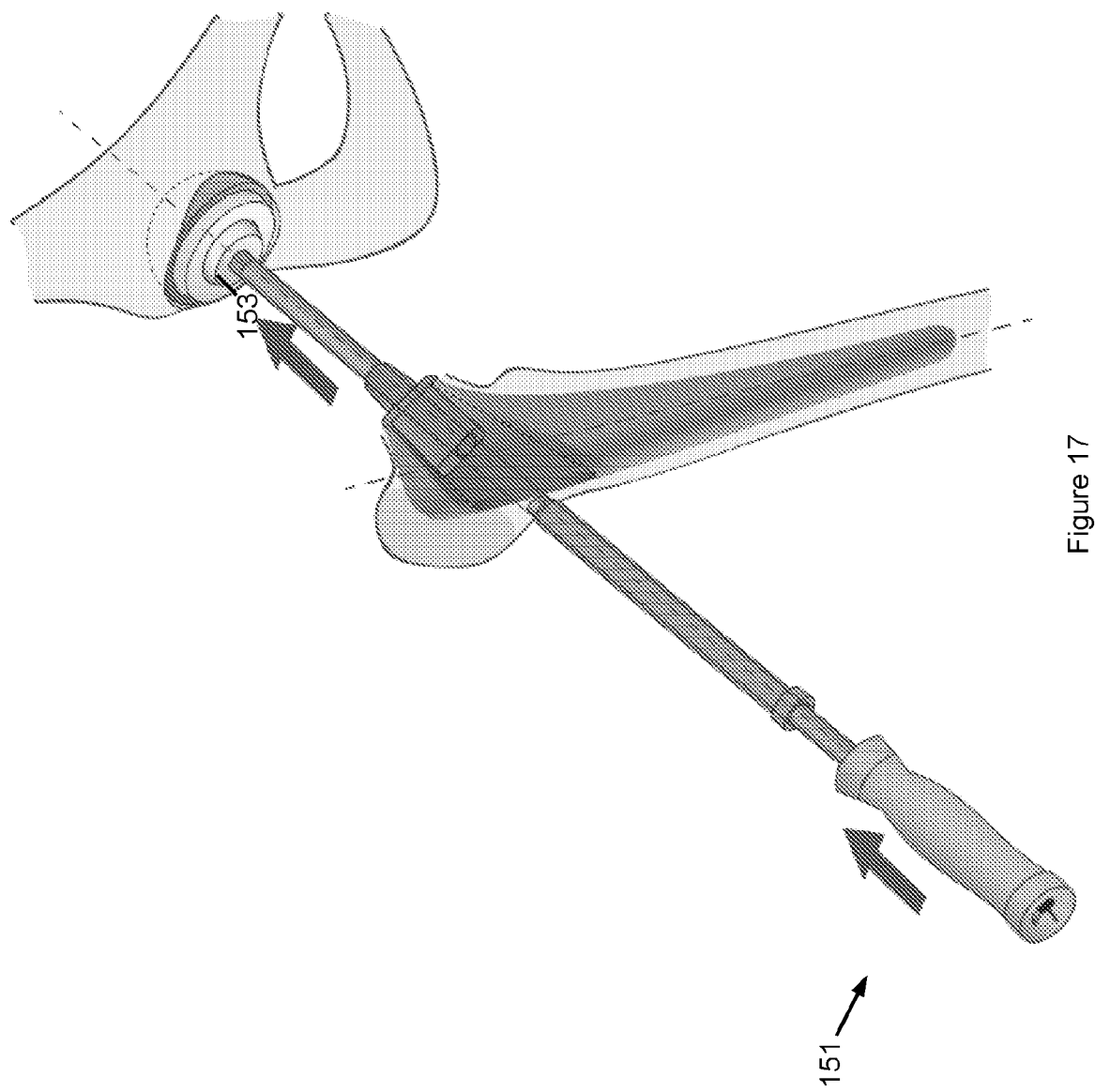

Having fixed the implant 142, a real or trial liner 152 may be inserted as is shown in FIG. 16. The impactor rod 172 may engage a trial head 153 to seat the liner 152. FIG. 17 shows the impaction of the impactor rod 172 to force the liner 152 into the cup 142 using the head 153.

Figure 18:
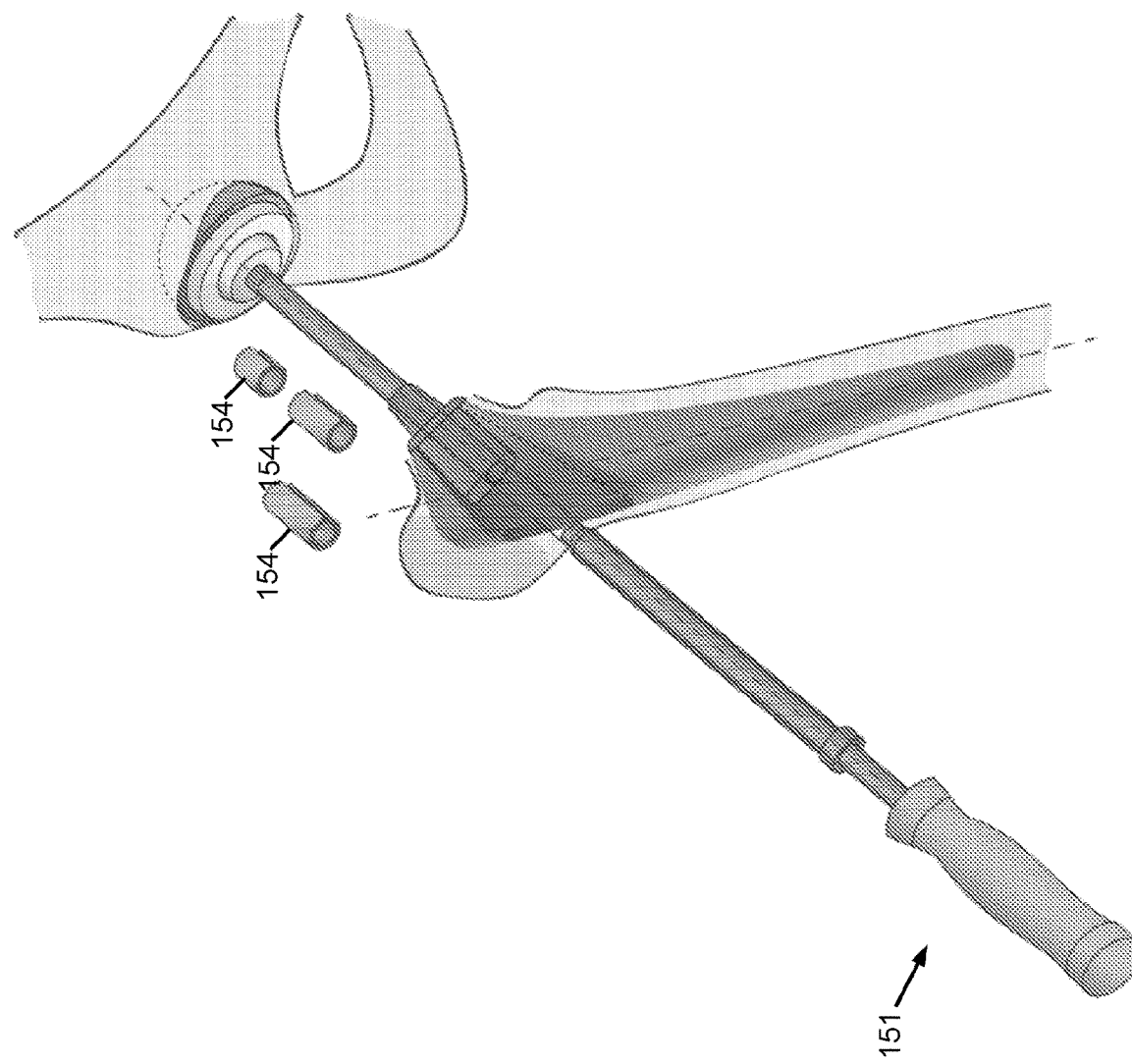
FIGS. 18-19 illustrates trial reduction utilising a plurality of offset spacers in accordance with an embodiment.

Trial reduction may now be performed. FIG. 18 illustrates the utilisation of measurement trial inserts 154 to trial differing component lengths for optimising leg length, offset, stability and the like.

The measurement trial inserts 154 may be cylindrical and lengthwise openable to clip about the shaft of the impactor rod 172. Furthermore, a plurality of trial inserts 154 comprising differing lengths may be provided such as comprising lengths of 5, 10, 13 mm and the like.

Figure 19:
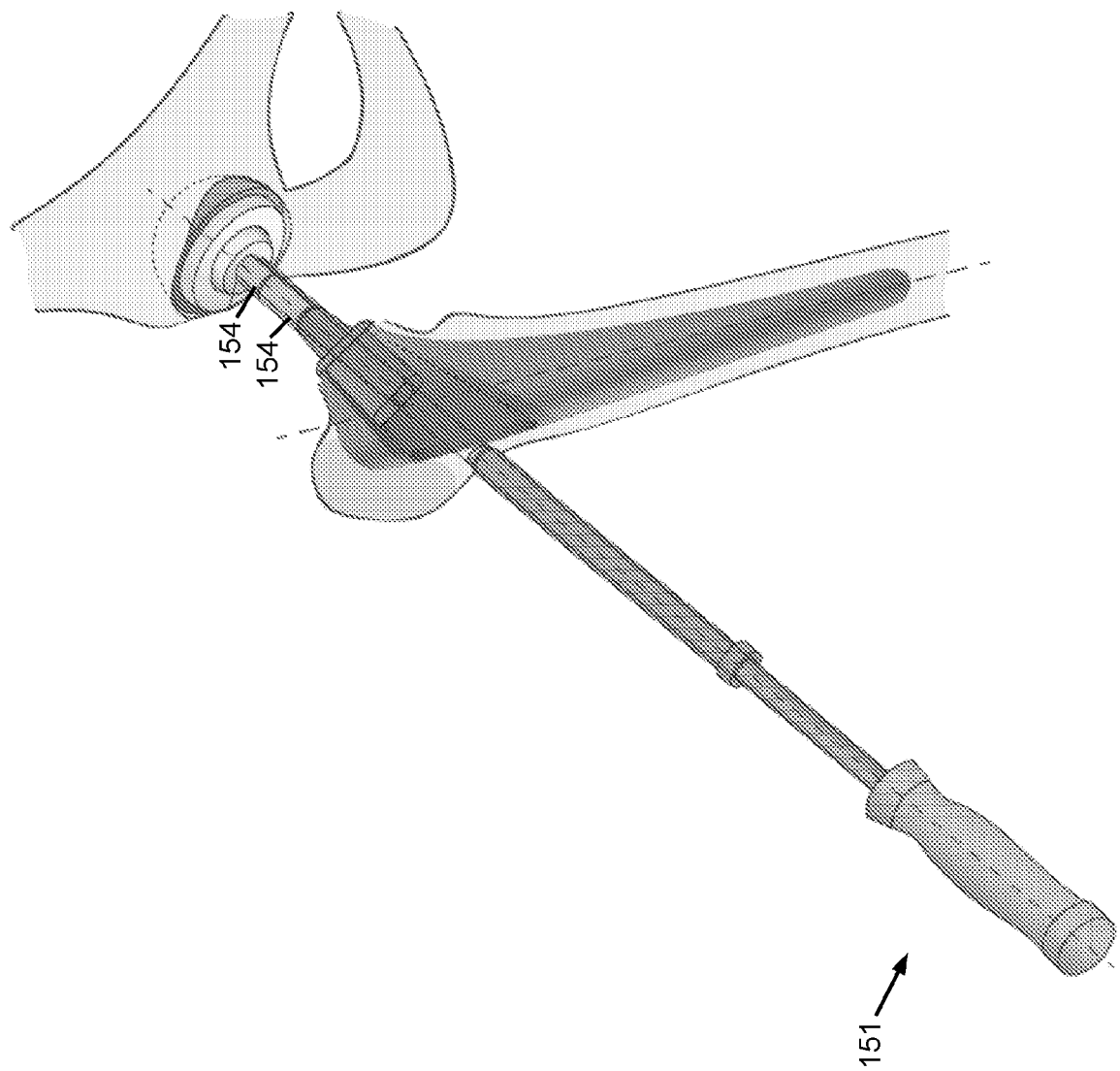

FIG. 19 illustrates the in-line insertion of two trial inserts 154 along the impactor rod 172 between the insert guide 113 and the cup 142.

Figure 20:
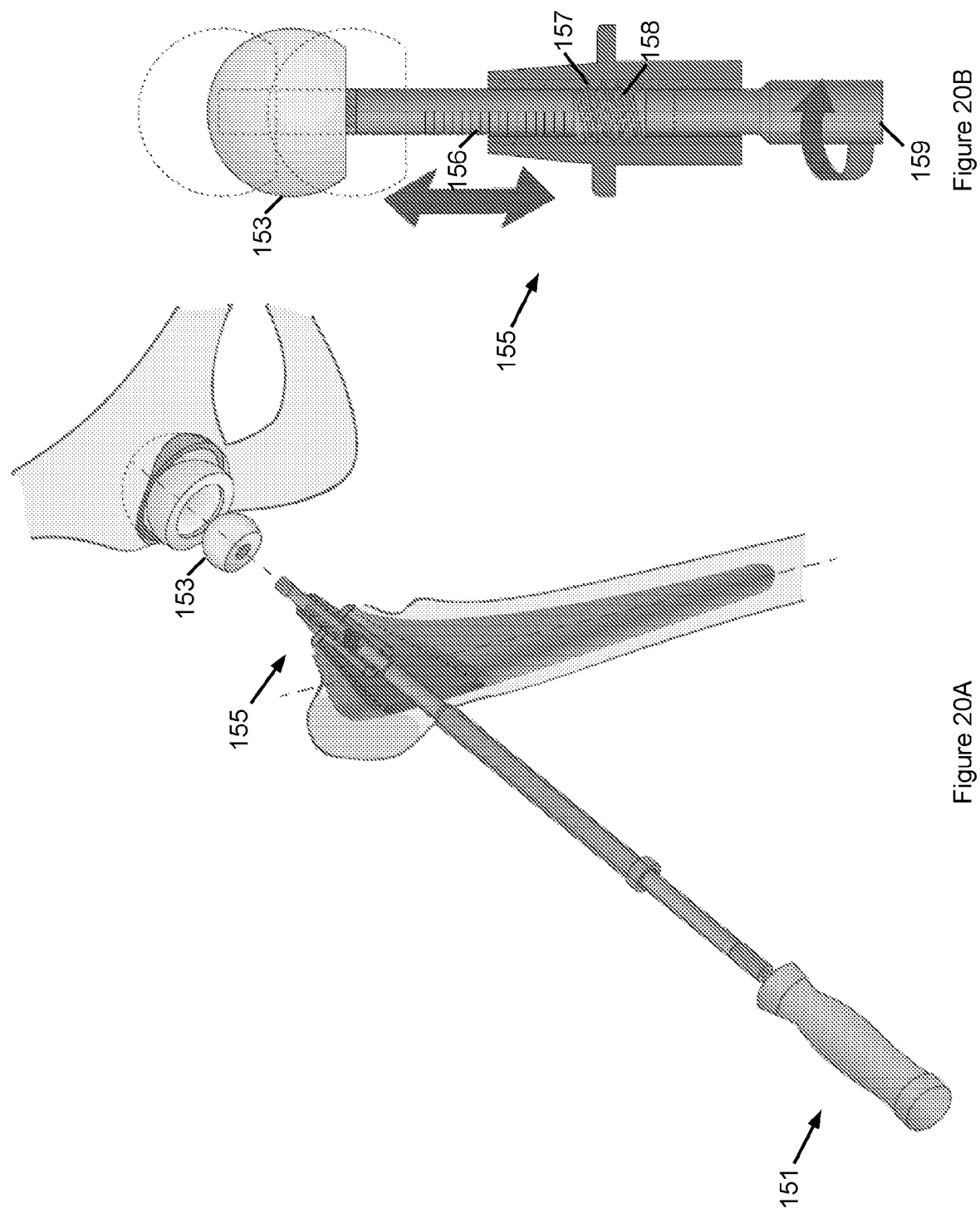
FIGS. 20 and 21 illustrates trial reduction utilising a screw adjustment bore insert mechanism in accordance with an embodiment.

FIG. 20 shows alternative trial reduction apparatus wherein an offset adjustable insert 155 comprising an interior thread 157 rotatably engaging corresponding threads 158 of a threaded rod 159 is located within the bore 110 of the broach 109.

As such, rotation of the threaded rod 159 with respect to the insert 155 adjusts the length and offset of the trial head 152.

Alternatively, a separate attachment can be inserted onto the broach insert 155.

Figure 21:
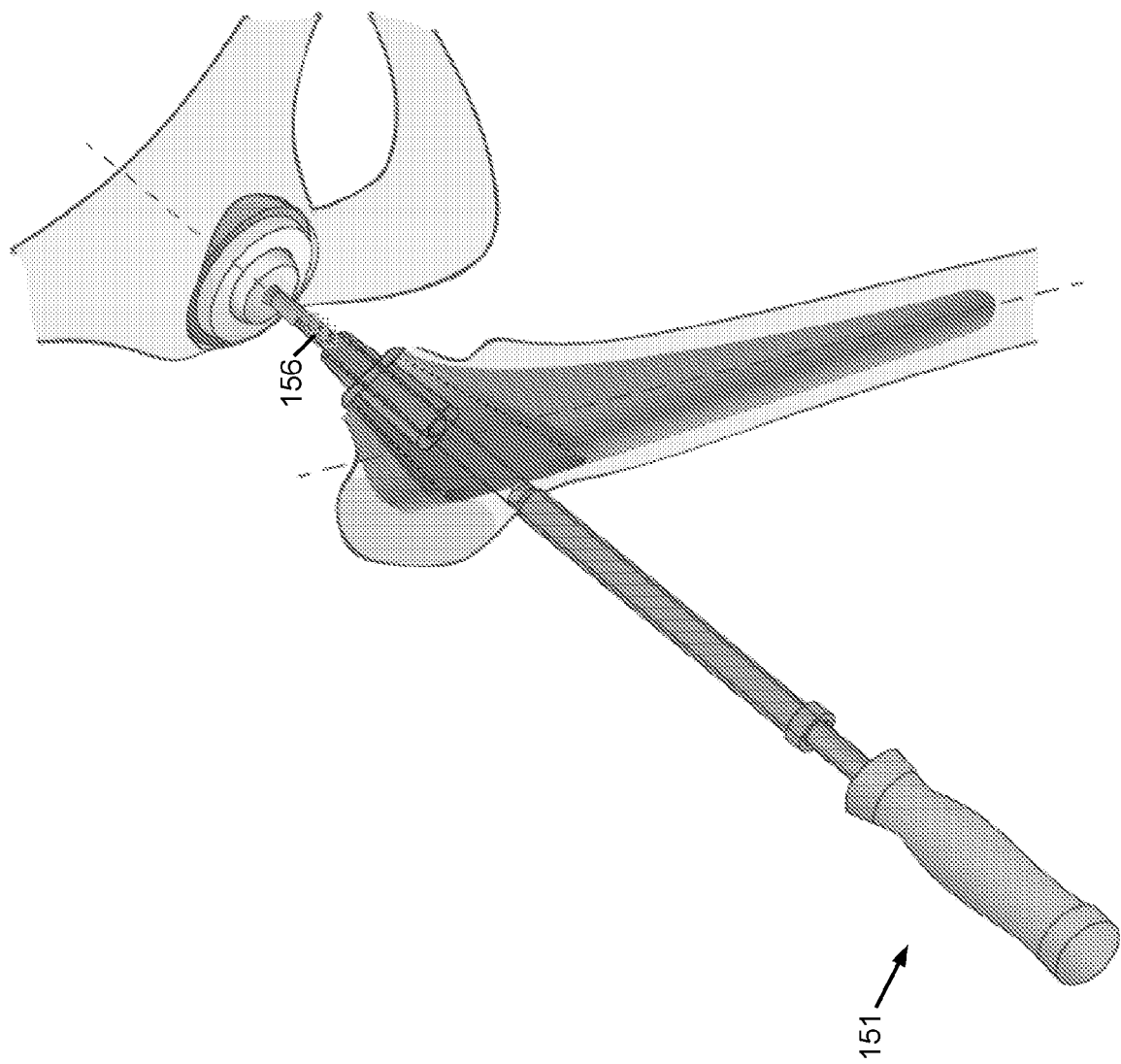

As is shown in FIG. 21, the threaded rod 159 may comprise markings 156 which may show the length in millimetres. As such, the threaded rod 159 is rotated to achieve the desirous length and offset upon which the reading is noted from the markings 156.

The trial reduction performed in accordance with the apparatus shown in FIG. 19 or 20 and 21 negates the conventional step of having to dislocate the hip for insertion of differing trial heads and neck lengths.

Figure 22B:
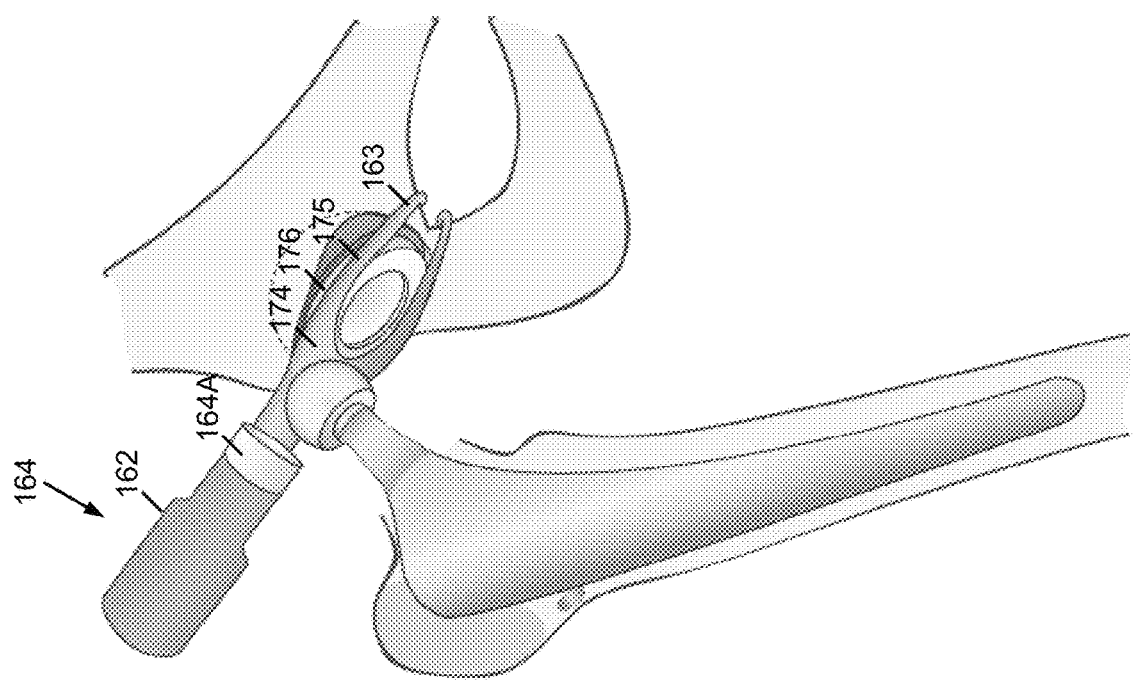
FIGS. 22-23 illustrates the illustrates the utilisation of a reduction device for guidance of a femoral component head into the acetabular component liner in accordance with an embodiment.
Figure 22A:
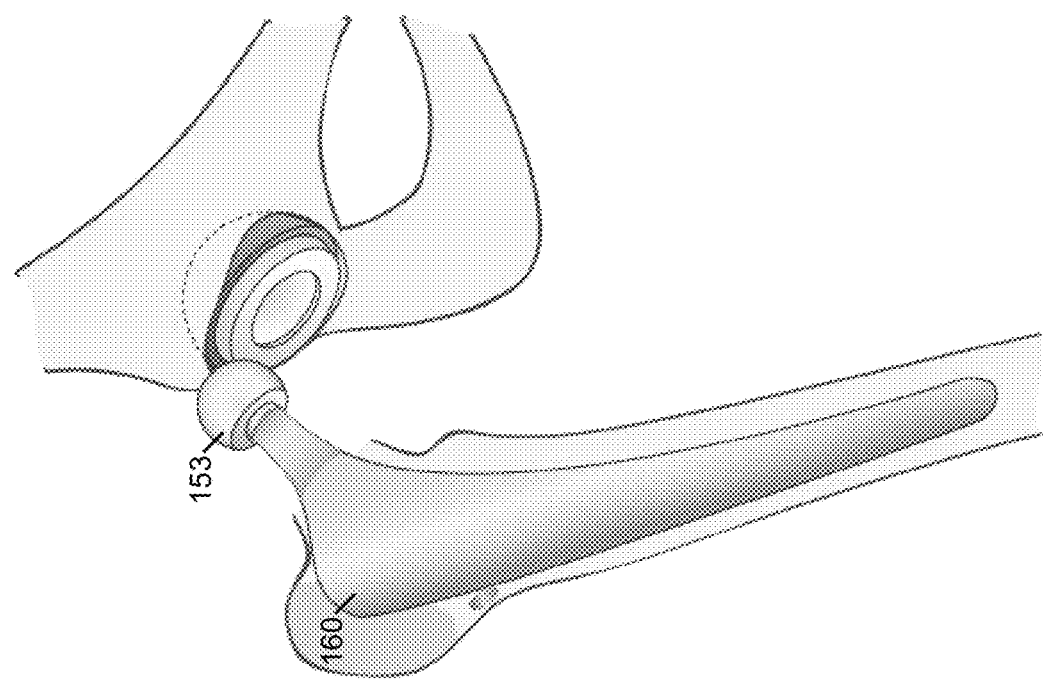
Figure 23B:
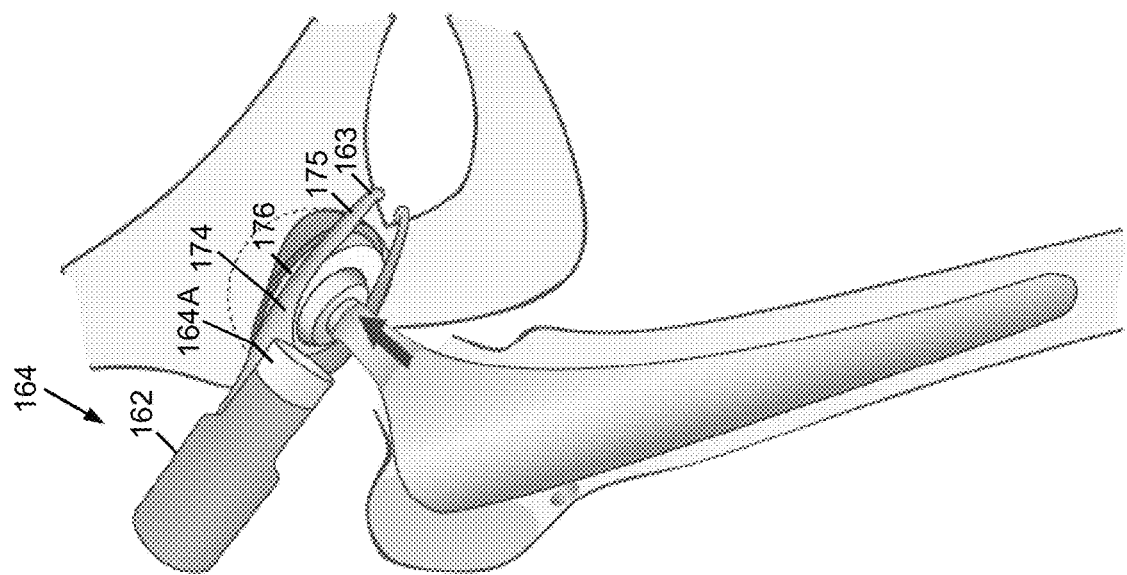
Figure 23A:
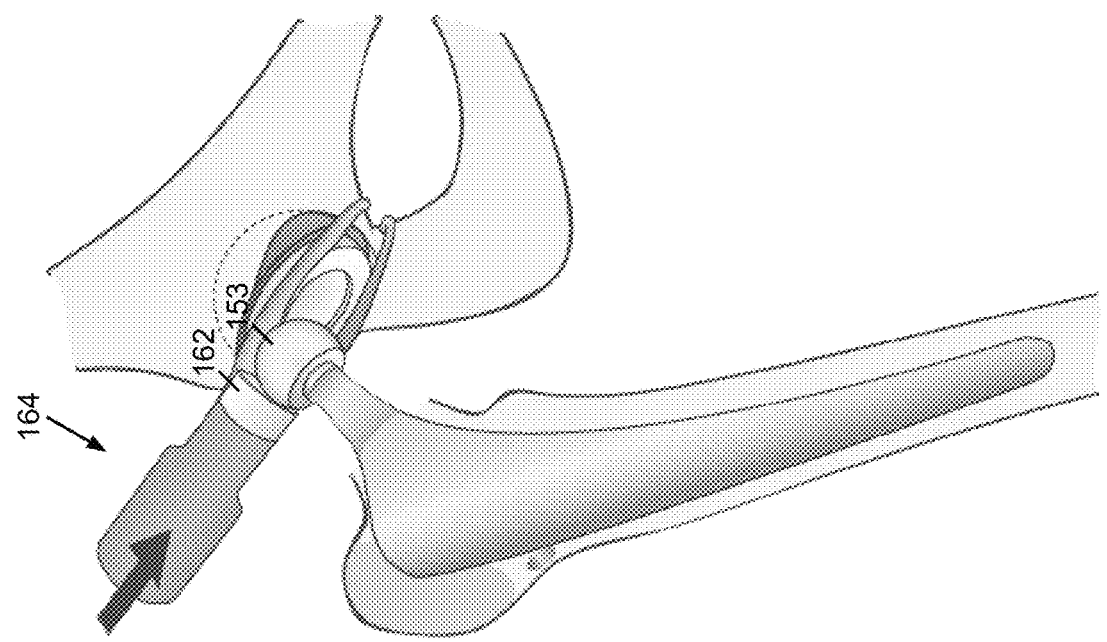

FIG. 22 illustrates the removal of the femoral broach 109 and the replacement therewith with the actual implant 160.

FIG. 22B illustrates the utilisation of a reduction device 164 to guide the implant head 161 into the liner 152 in an embodiment. The reduction device 164 may comprise a fork 176 that may comprise a pair of divergent tines 175 that diverge from a stem plate 174 about the entrance to the liner 152. Distal ends of the forks 176 may comprise engagements 163 that engage the pelvis foramen or the inferior edge of the cup 142. In embodiments, a countertraction mechanism located within the liner, such as a ball located within the liner (not shown) may be displaced when the real head 153 is inserted.

The femoral component head 153 may initially be located against the stem plate 174 to as to be able to slide therealong. The stem plate 174 may be lengthwise concave so as to bias the head 153 centrally.

The reduction device 164 may further comprises a handle 162 which is offset adjustable with respect to the fork 176, such as by utilising a screw, ratchet mechanism or the like. As such, having located the implant head 161 against the stem plate 174, the handle 162 is offset towards the fork 176 such that a bearing head 164A abuts against the implant head 161 and pushes the implant head 153 along the stem 174 towards the entrance of the liner 152 as a substantially shown in FIG. 23A until such time that the implant head 161 locates into the liner 152 between the tines 175 as a substantially shown in FIG. 23B.

Figure 24:
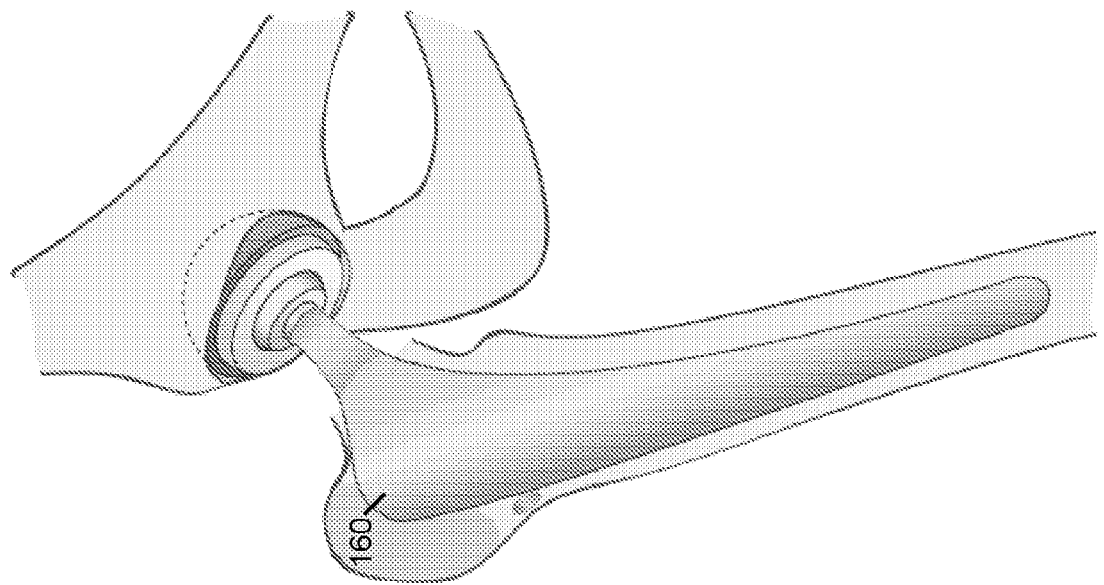
FIG. 24 illustrates a resurfaced hip joint.

FIG. 24 shows the completed resurfaced hip joint 100.

Figure 25:
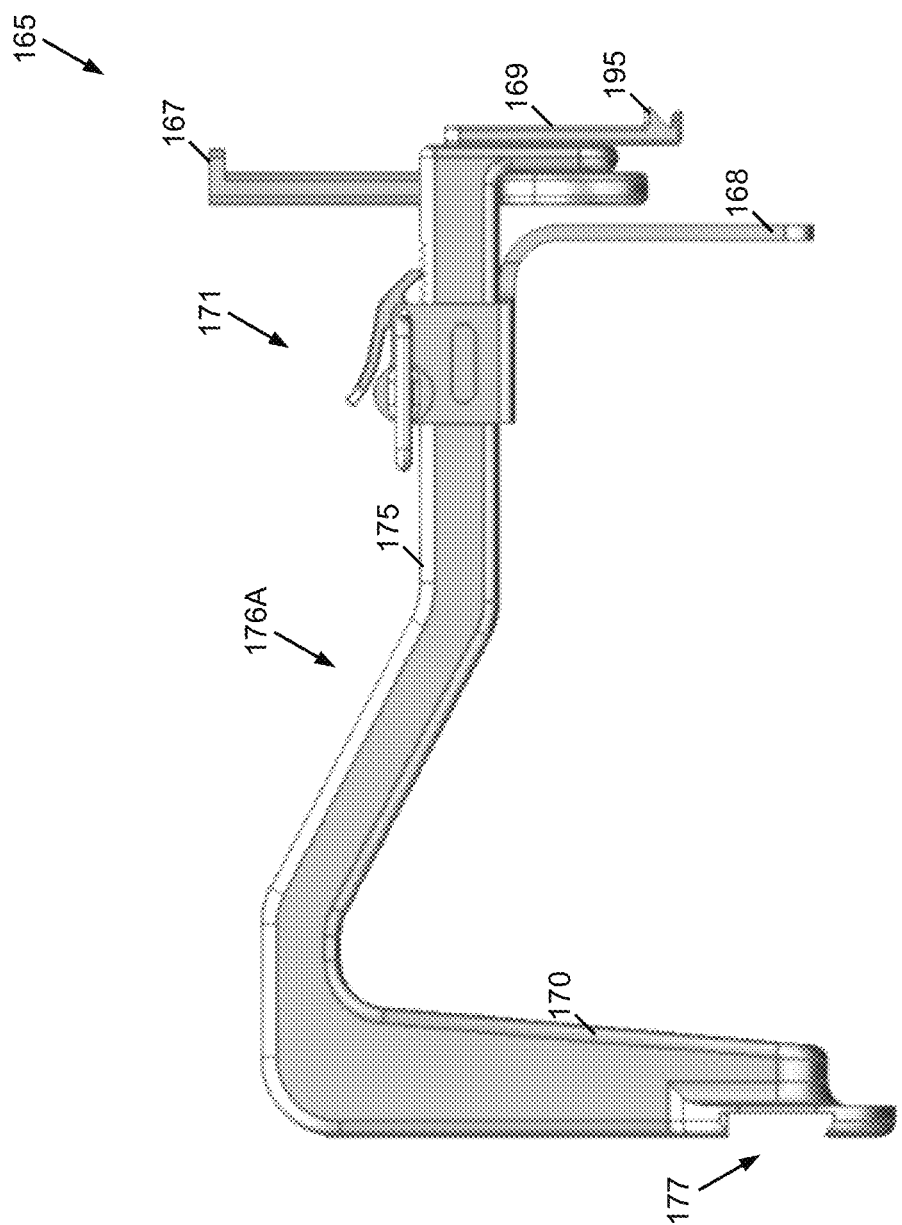
FIG. 25 illustrates an arthroplasty jig in accordance with an embodiment.

FIG. 25 shows an arthroplasty jig 165 for present techniques configured for both distraction and driving in an embodiment.

The arthroplasty jig 165 may comprise a rigid frame 176A which may comprise a spine 175 and an orthogonal proximal handle 170 which, in embodiments, may adjoin the spine 175 via a curved transition. The distal end of the proximal handle 170 may comprise an insert accommodation 177.

The spine 175 may support an orthogonal femoral distraction arm therealong 168 by way of a ratchet and pawl mechanism or other mechanisms 171.

The spine 177 may further support an orthogonal pelvic distraction arm 169 that opposes the femoral distraction arm 168 to distract the femur 101 from the acetabulum 106.

The distraction arm 169 may be orthogonally adjustable between engaged and disengaged positions in the manner described below. The medial face of the distal end of the pelvic distraction arm 169 may comprise a semi-spherical groove 195 for engaging the rim of the acetabulum 106.

The spine 177 may further support an orthogonal drive arm 167 which locates between the distraction arms 168, 169. The orthogonal drive arm 169 may be similarly orthogonally offset adjustable between disengaged and engaged positions.

Figure 26B:
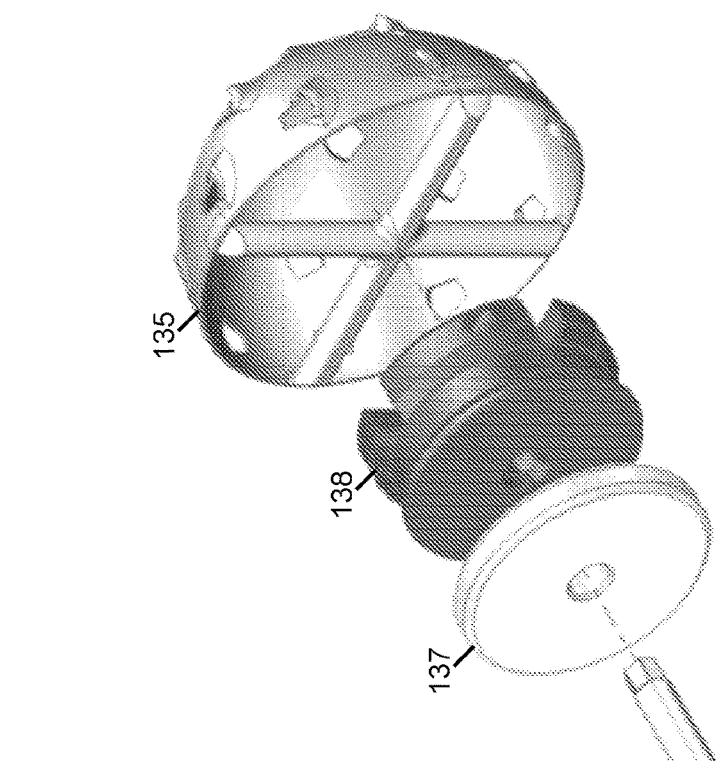
FIG. 26-27 illustrate the use of the arthroplasty jig for reaming in accordance with an embodiment.
Figure 26A:
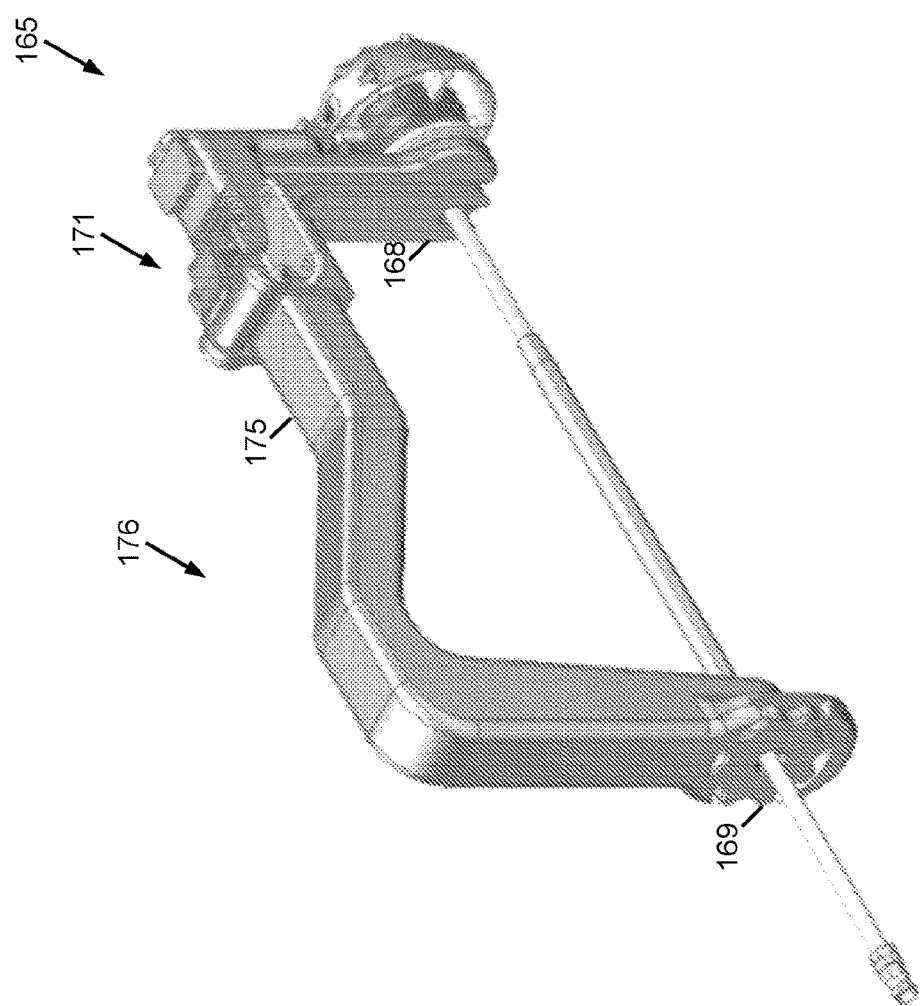

FIG. 26 illustrates the utilisation of the arthroplasty jig 165 for reaming. Specifically, there is shown the engagement of the reaming rod 141 at the proximal end via an aperture of an insert 169 within the insert accommodation 177 of the proximal handle 170. The insert 169 stabilises the rod 141 by being one of 3 points of fixation for accurate reaming.

The distal end of the reaming rod 141 is engaged within the notches 134 (or apertures or the like) of the distal ends of the femoral distraction arm 168 and the drive arm 167. The drive arm 167 is shown in the engaged position.

FIG. 26B shows the engagement of the cutting head 135, adapter plate 138 and proximal bearing plate 137.

Figure 27B:
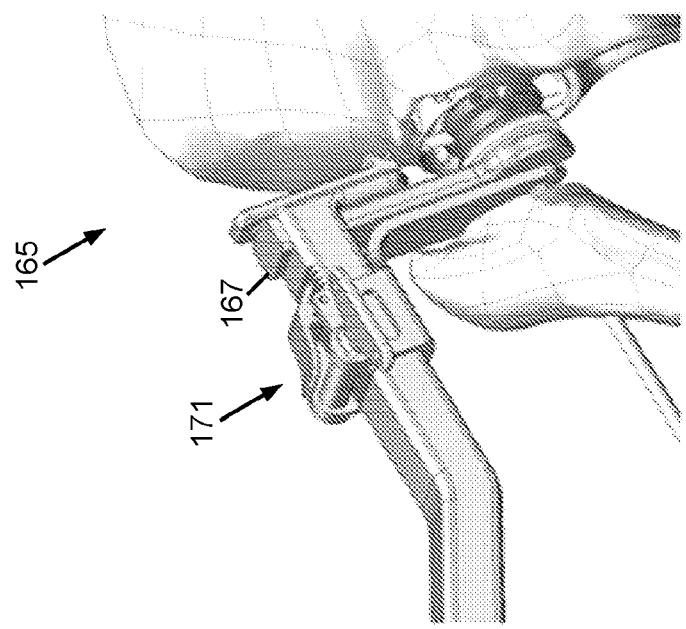
Figure 27A:
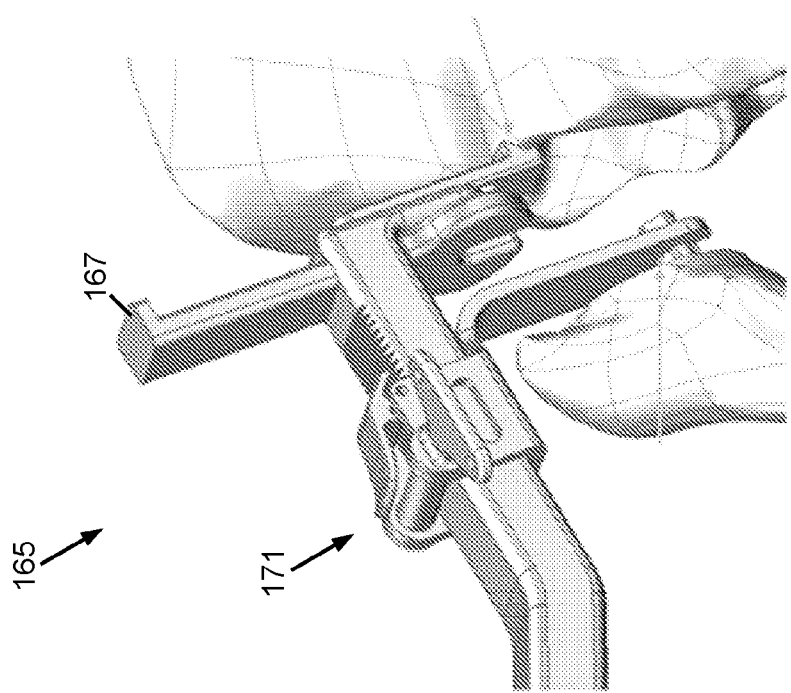

FIG. 27 shows the utilisation of the arthroplasty jig 165 further. Specifically, FIG. 27A shows the offset of the femoral distraction arm 168 away from the pelvic distraction arm 169 to distract the femur 101 from the acetabulum. A turnkey of the ratchet and pawl mechanism 171 or other mechanism may be rotated to offset the femoral distraction arm 168 away from the pelvic distraction arm 169. The drive arm 167 is shown as disengaged.

The medial facing acetabulum rim engaging groove 195 of the pelvic distraction arm 169 may engage the rim of the acetabulum 106.

In embodiments, the jig 165 has no femoral distraction arm 168. In this embodiment, the lateral face of the drive arm 169 may abut against the medial face of the femoral broach 109.

When the femur is distracted, the cutting head 135 and associated componentry may be fastened to the distal end of the reaming rod 144.

Thereafter, the drive arm 167 may be engaged by orthogonal downward transition such that the distal end thereof locates behind the bearing plate 137 and the reaming rod 141 is engaged within the notch 134.

The ratchet and pawl mechanism 171 may then be released such that the pelvic distraction arm 169 may be disengaged from the acetabulum and moved orthogonally to the disengaged position shown in FIG. 27B.

The acetabulum 106 may then be reamed by applying force to the proximal handle 171 which drives the cutting head 135 via the engaged drive arm 167. The reaming rod 141 is rotated simultaneously to rotate the cutting head 135.

Figure 28B:
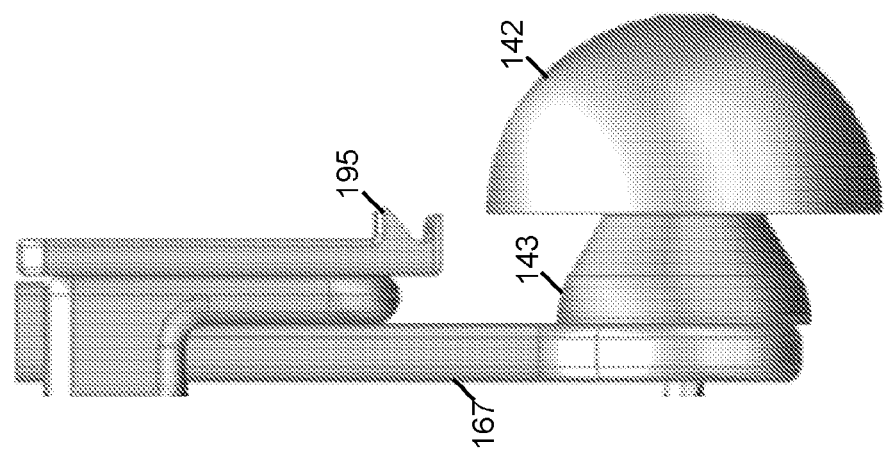
FIGS. 28 and 29 illustrate the use of the arthroplasty jig for impaction in accordance with an embodiment.
Figure 28A:
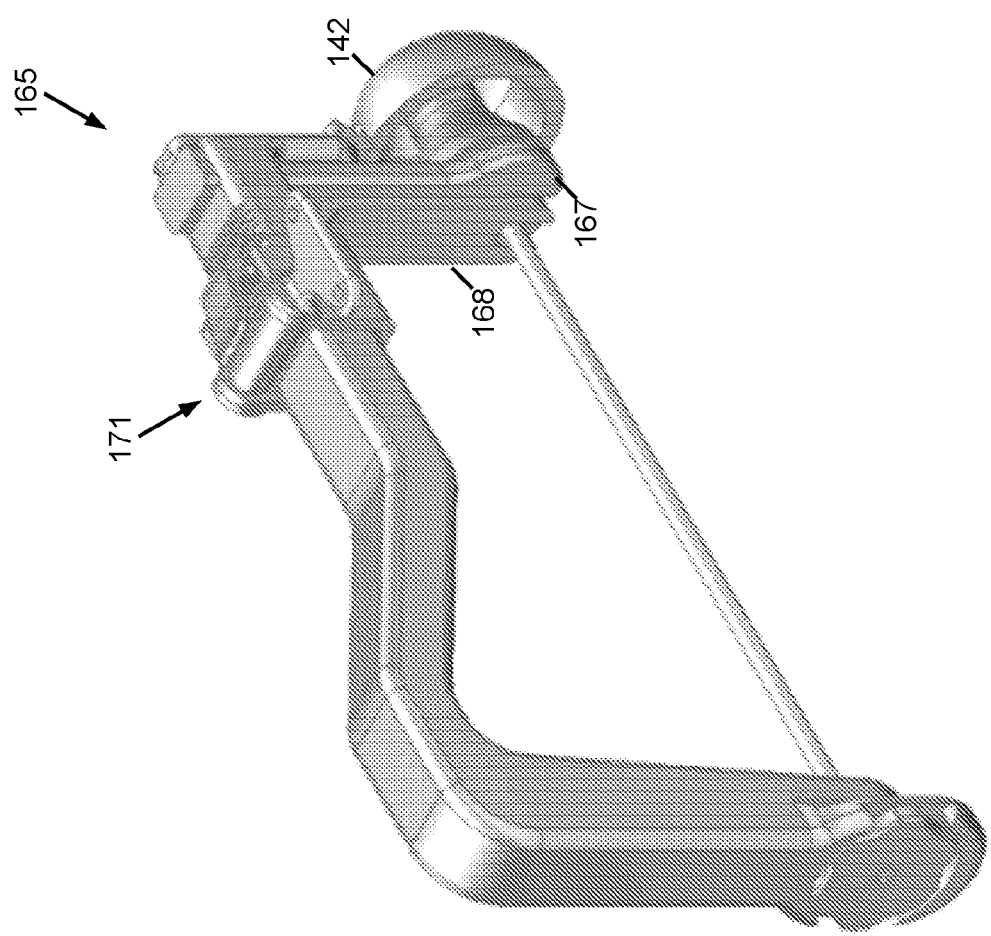

FIG. 28 shows the utilisation of the arthroplasty jig 165 for cup impaction wherein the jig 165 similarly supports the impactor rod 172, the conical adapter 143 and the implant 142.

Figure 29:
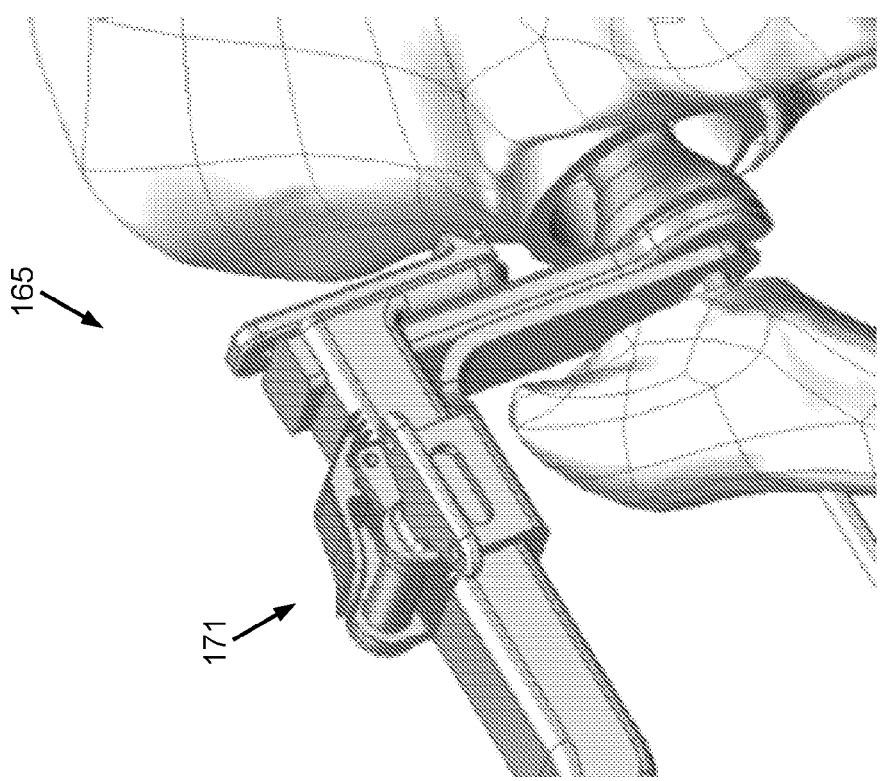

As is shown in FIG. 29, during impaction, the pelvic distraction arm 169 may be disengaged and the femoral distraction arm 168 released such that the proximal face of the proximal handle 170 may be struck to impact the implant 142 into the acetabulum 106 via the drive arm 167.

Figure 30:
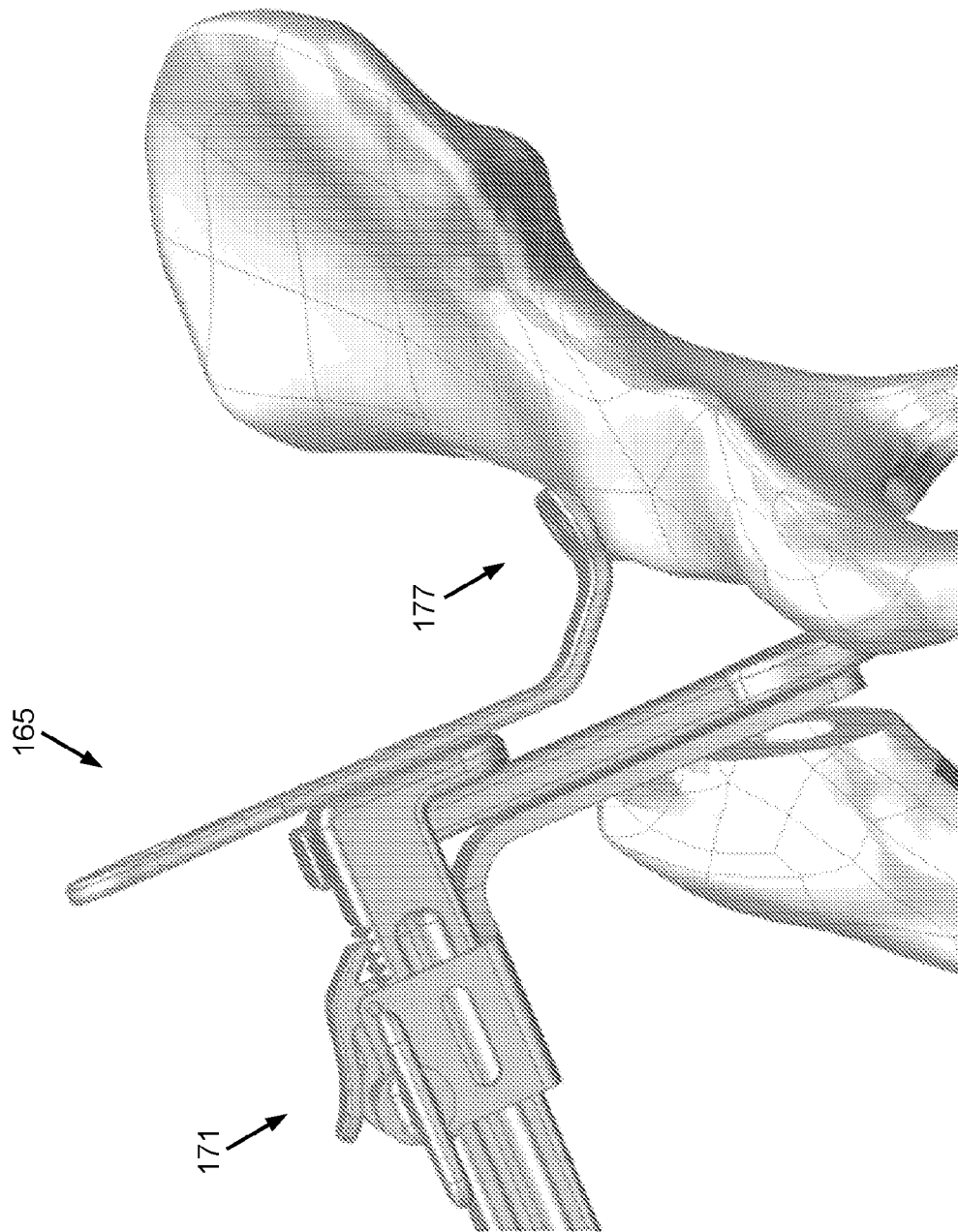
FIG. 30 illustrates a variation of the arthroplasty jig wherein a distal end of a pelvic distraction arm thereof is fixated directly to the pelvis in accordance with an embodiment.
Figure 31B:
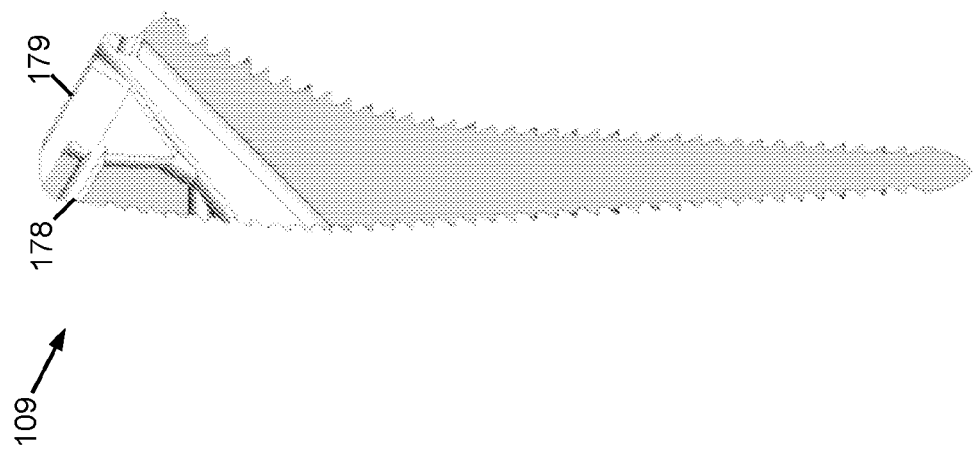
FIG. 31 illustrates the femoral broach in further detail in accordance with an embodiment.
Figure 31A:
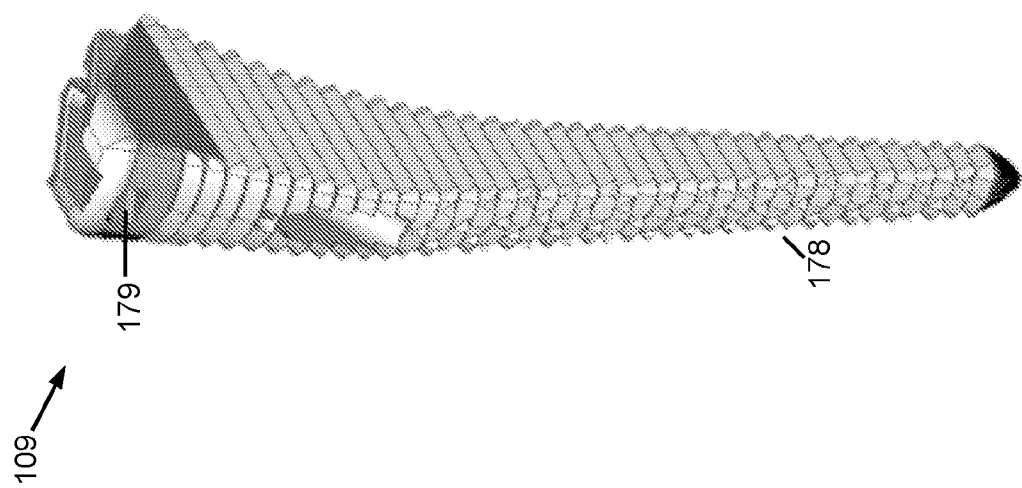

FIG. 30 illustrates an embodiment wherein the pelvic distraction arm 169 rather comprises a pelvic attachment plate 177 which may be fastened to the pelvis 102 utilising fixation screws, pins or the like as opposed to engaging the rim of the acetabulum as described above.

A superior end of the femoral broach 109 may comprise a femoral hammer engagement entrance port 179 and orthogonal latch port 178 for engaging the broach handle 112 in the manner substantially illustrated in FIG. 32. Specifically, FIG. 32A shows the distal end of the handle 112 comprising an insertion end 181 that locates within the entrance port 179. An orthogonal latch 180 selectively extends into the orthogonal latch port 178 from about pivot 182. The latch 180 is disengageable by depressing accessible detent arm 183 and reset by biasing arm 184.

Figure 33:
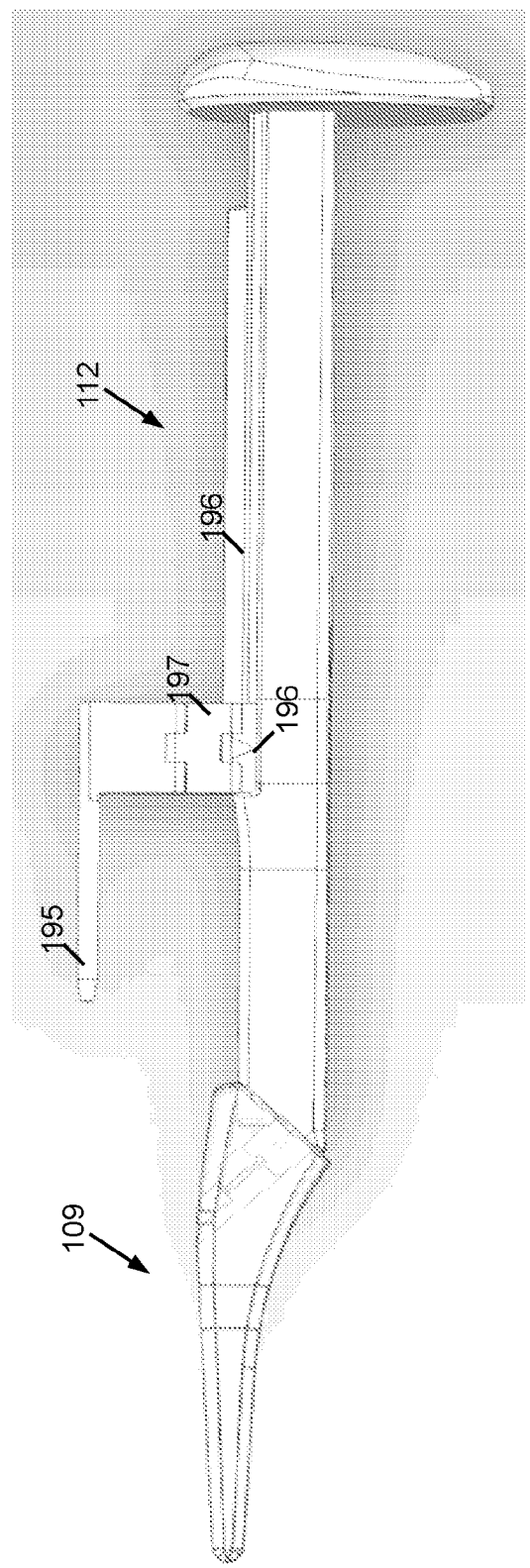
FIG. 33 shows the broach handle engaging the femoral broach in accordance with a further embodiment.

FIG. 33 further shows an embodiment of the handle 112 comprising a greater trochanter 108 referencing depth guide 195. The depth guide 195 may be slidable along a track 196 to differing positions which may be read from a scale 196. Offset inserts 197 may space the depth guide 195 laterally according to patient bone geometry.

Figure 34B:
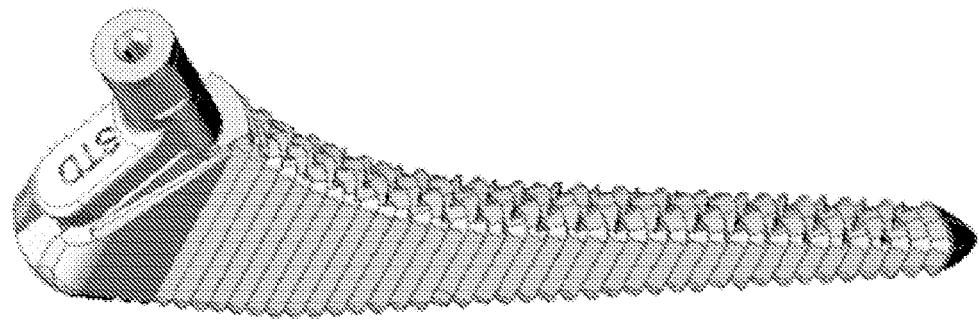
FIG. 34 illustrates the femoral broach in accordance with a further embodiment.
Figure 34A:

FIG. 34 shows an embodiment wherein the broach insert 113 comprises a flange 183 that covers the entrance port 179. Furthermore, the insert 113 may selectively engage a guide wire insert 182 of smaller inner diameter. The guide wire insert 182 may be utilised for the initial guidance of the guide wire 123 and subsequently removed from the cannulated reaming and drive rods 144.

Figure 35:
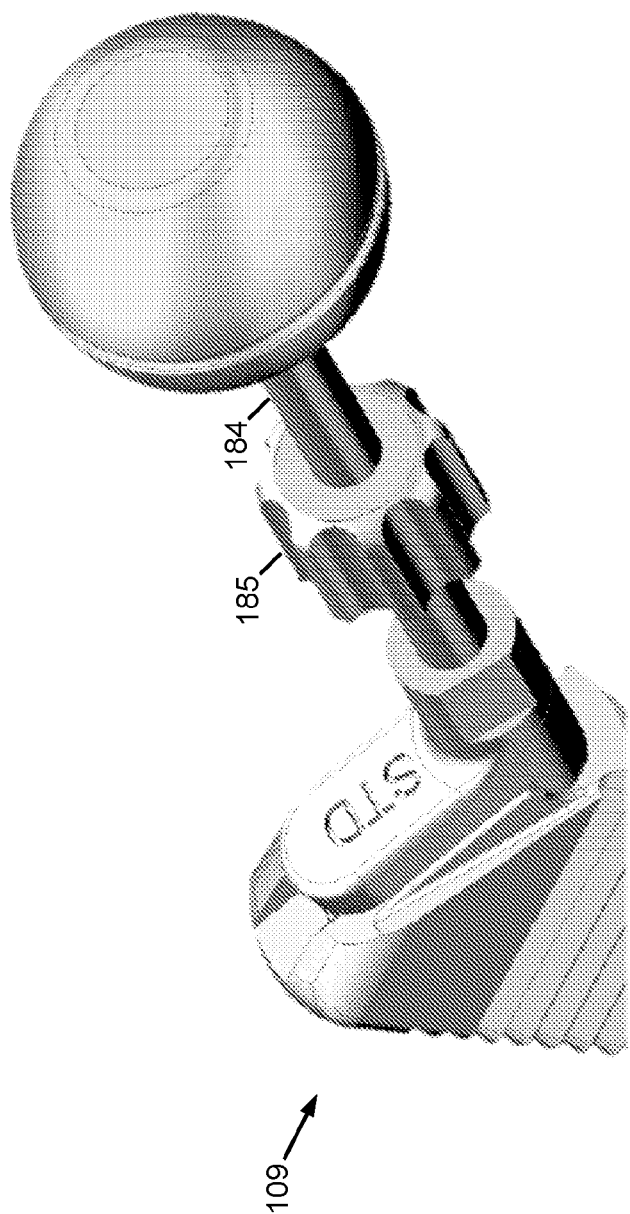
FIG. 35 illustrates length adjustable trial neck component in accordance with an embodiment.

FIG. 35 illustrates a trial stem rod 184 for trial reduction and finger grip barrel 185 that screwably locates within or over the insert 113 for tightening. Within 185 can be internal threads such that when the rod 184 is rotated it will adjust the length and offset of the rod 184 from the insert 113. This removes the requirement to dislocate the hip each time to trial different length trial heads.

Figure 36:
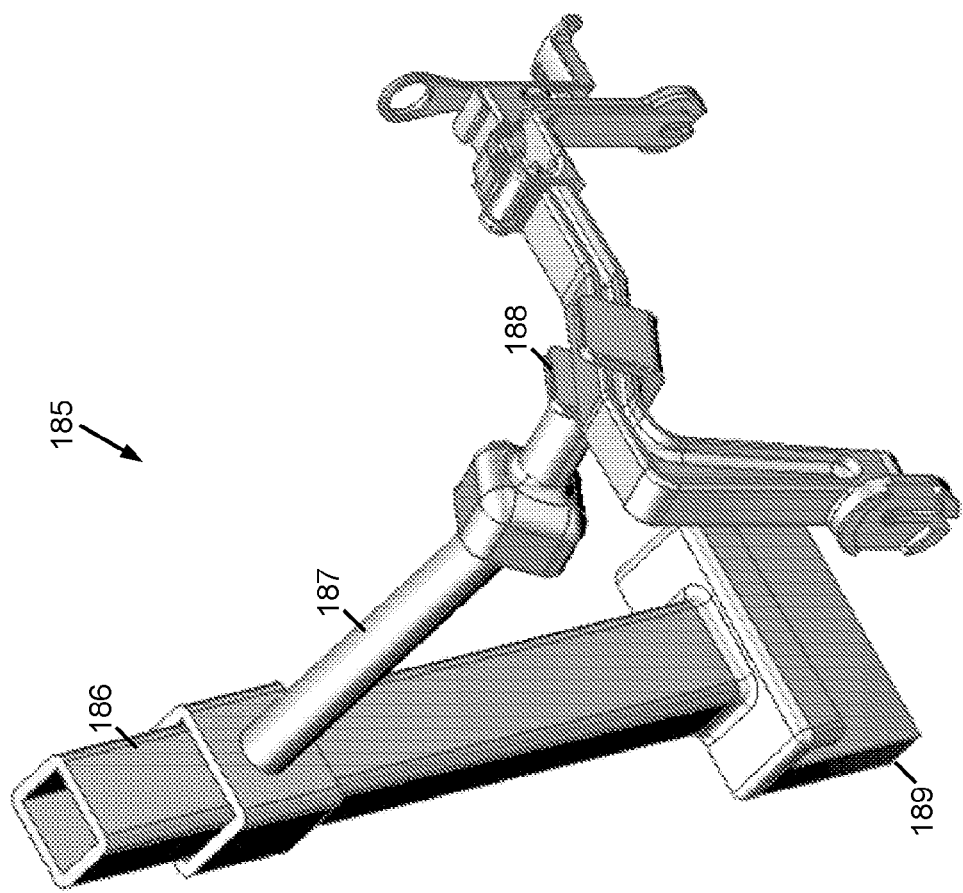
FIG. 36 shows an arthroplasty jig securement in accordance in an embodiment.

FIG. 36 illustrates an arthroplasty jig 165 securement comprising a support post 186 which is clamped to the operating table (not shown) utilising distal clamp 189. An orthogonal support arm 187 slidably engages the support post 186 which comprises a distal hand 188 which engages the spine 175 of the jig 165.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. Whereas the present techniques and apparatus have been described primarily with reference to hip joint arthroplasty, such may be applied to other joints also in embodiments. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A method for performing hip arthroplasty involving a femur having a femoral shaft, neck and head and an adjacent pelvis having an acetabulum formed thereon, the method comprising:
   intramedullary insertion of an elongate femoral broach into the shaft, the broach comprising a superior lateromedial transverse bore;

locating a reaming rod through the transverse bore and femoral neck;

coupling a cutting head to a distal end of the reaming rod via an incision; and rotating the cutting head using the reaming rod to ream the acetabulum.

2. The method as claimed in claim 1, further comprising:

inserting an orthogonal drive arm of an arthroplasty jig to locate and operatively press behind the cutting head; and driving the cutting head using the drive arm.

3. The method as claimed in claim 2, wherein the method further comprises removing the cutting head and attaching an implant to a distal end of an impactor rod located through the bore via an implant adapter and striking an orthogonal proximal handle of the arthroplasty jig to drive the implant into the acetabulum via the drive arm.

4. The method as claimed in claim 3, further comprising screwing fixation screws through the implant utilising a screw driver inserted via the bore.

5. The method as claimed in claim 4, wherein a distal end of the screwdriver is flexible.

6. The method as claimed in claim 4, wherein the method comprises manipulating the femur to position the distal end of the screwdriver.

7. The method as claimed in claim 3, further comprising trial reduction comprising insertion of a liner within the implant and location of trial inserts of differing lengths along a trial reduction rod between the broach and a trial head located within the implant.

8. The method as claimed in claim 3, further comprising trial reduction comprising insertion of a liner within the implant and insertion of a screw rod screwably engaged to the broach, the screw rod having a trial head at a distal end thereof and rotating the screw rod with respect to the broach to adjust the length and offset of the trial head away from the broach.

9. The method as claimed in claim 3, further comprising removal of the broach and the intramedullary insertion of an implant.

10. The method as claimed in claim 9, further comprising engaging diverging tines of a fork of a reduction device about an entrance of a liner inserted within the implant and locating a head of the implant against a stem of the fork and adjusting a bearer of the device with respect to the fork to push the head towards the liner entrance.

11. The method as claimed in claim 10, wherein distal ends of the diverging tines engage at least one of an inferior edge of the implant and the pelvic foramen.

12. The method as claimed in claim 2, wherein the arthroplasty jig further comprises a femoral distraction arm and a pelvic distraction arm and wherein the method further comprises distracting the femur away from the pelvis by offsetting the femoral distraction arm away from the pelvic distraction arm.

13. The method as claimed in claim 12, wherein the orthogonal drive arm is orthogonally transitionable between disengaged and engaged positions and wherein the method further comprises engaging the orthogonal drive arm behind the cutting head and around the reaming rod and disengaging a locking mechanism to relax the femoral distraction arm towards the pelvic distraction arm.

14. The method as claimed in claim 1, wherein locating the reaming rod comprises:

drilling of a guide wire through the transverse bore and femoral neck and head;

following the guide wire with a cannulated overdrill to form a femoral neck passage;

removing the cannulated overdrill; and following the guide wire with the reaming rod.

15. The method as claimed in claim 14, wherein the femoral neck passage comprises a diameter of less than 10 mm.

16. The method as claimed in claim 14, wherein the femoral neck passage comprises a diameter of between 3 and 8 mm.

17. The method as claimed in claim 14, wherein the femoral neck passage comprises a diameter of less than 6 mm.

18. The method as claimed in claim 14, wherein the femoral neck passage comprises a diameter of between 4 mm and 6 mm.

19. The method as claimed in claim 14, further comprising drilling the guide wire mediolaterally through the bore utilising a curved guidance tube.

20. The method as claimed in claim 1, further comprising inserting the femoral broach utilising a femoral handle.

21. The method as claimed in claim 20, further comprising controlling the insertion depth of the femoral broach utilising an insertion depth referencer on the femoral handle.

22. The method as claimed in claim 21, wherein the insertion depth referencer comprises a depth referencing pin referencing the femur, the depth referencing pin being orthogonal with an intramedullary axis of the femur.

23. The method as claimed in claim 22, wherein the depth referencing pin references the greater trochanter of the femur.

24. The method as claimed in claim 20, further comprising attaching a referencing guidance jig to the femoral handle and wherein the referencing guidance jig comprises a position regulator and wherein the method comprises guiding a guide wire lateromedially towards the bore through an aperture of the position regulator.

25. The method as claimed in claim 24, wherein the position regulator comprises a plurality of apertures and wherein the method further comprises selecting one of the apertures according to a desirous insertion angle.

26. The method as claimed in claim 1, wherein the bore has a cross-section parallel an elongate axis of the broach and wherein the cross-section is wider along the elongate axis.

27. The method as claimed in claim 26, wherein the bore tapers latermedially.

28. The method as claimed in claim 26, wherein the bore defines a lateral entrance and a medial exit and wherein the method further comprises placing a guide wire insert having a guide bore into the bore exit and guiding a guide wire through the guide bore.

29. The method as claimed in claim 28, wherein the method further comprises selecting the guide wire insert from a selection of guide wire inserts according to a guide bore angle.

30. The method as claimed in claim 1, further comprising adjusting an orientation of the femoral shaft to adjust a reaming angle of the reaming rod.

31. The method as claimed in claim 30, further comprising orientating the femoral shaft parallel with the ground.

\* \* \* \* \*